US012594424B2

(12) United States Patent
Steinke et al.

(10) Patent No.: US 12,594,424 B2
(45) Date of Patent: Apr. 7, 2026

(54) SYSTEMS AND METHODS FOR ESTIMATING A VOLUME OF ACTIVATION USING A COMPRESSED DATABASE OF THRESHOLD VALUES

(71) Applicant: Boston Scientific Neuromodulation Corporation, Valencia, CA (US)

(72) Inventors: G. Karl Steinke, Valencia, CA (US); Richard Mustakos, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1008 days.

(21) Appl. No.: 17/731,190

(22) Filed: Apr. 27, 2022

(65) Prior Publication Data

US 2022/0249847 A1 Aug. 11, 2022

Related U.S. Application Data

(63) Continuation of application No. 15/937,264, filed on Mar. 27, 2018, now Pat. No. 11,357,986.

(Continued)

(51) Int. Cl.
*A61N 1/36* (2006.01)
*A61N 1/02* (2006.01)
(Continued)

(52) U.S. Cl.
CPC ......... *A61N 1/36128* (2013.01); *A61N 1/025* (2013.01); *A61N 1/0534* (2013.01);
(Continued)

(58) Field of Classification Search
CPC .. A61N 1/36128; A61N 1/025; A61N 1/0534; A61N 1/36185; A61N 1/37247;
(Continued)

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 0813889 12/1997
EP 1048320 11/2000
(Continued)

OTHER PUBLICATIONS

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

(Continued)

*Primary Examiner* — Carl H Layno
*Assistant Examiner* — Maria Catherine Anthony
(74) *Attorney, Agent, or Firm* — Branch Partners PLLC; Bruce E. Black

(57) ABSTRACT

A system for estimating a volume of activation around an implanted electrical stimulation lead for a set of stimulation parameters includes a display; and a processor coupled to the display and configured to: receive a set of stimulation parameters including a stimulation amplitude and a selection of one of more electrodes of the implanted electrical stimulation lead for delivery of the stimulation amplitude; determine an estimate of the volume of activation based on the set of stimulation parameters using the stimulation amplitude and a database including a plurality of planar distributions of stimulation threshold values and a map relating the planar distributions to spatial locations based on the one or more electrodes of the implanted electrical stimulation lead selected for delivery of the stimulation amplitude; and output on the display a graphical representation of the estimate of the volume of activation.

20 Claims, 10 Drawing Sheets

Related U.S. Application Data

(60) Provisional application No. 62/480,942, filed on Apr. 3, 2017.

(51) Int. Cl.

| | |
|---|---|
| *A61N 1/05* | (2006.01) |
| *A61N 1/372* | (2006.01) |
| *G16H 20/40* | (2018.01) |
| *G16H 40/63* | (2018.01) |
| *G16H 50/70* | (2018.01) |

(52) U.S. Cl.
CPC ..... *A61N 1/36185* (2013.01); *A61N 1/37247* (2013.01); *A61N 1/37282* (2013.01); *G16H 20/40* (2018.01); *G16H 40/63* (2018.01); *G16H 50/70* (2018.01)

(58) Field of Classification Search
CPC .... A61N 1/37282; G16H 20/40; G16H 40/63; G16H 50/70
See application file for complete search history.

(56) References Cited

U.S. PATENT DOCUMENTS

| | | | |
|---|---|---|---|
| 4,177,818 | A | 12/1979 | De Pedro |
| 4,341,221 | A | 7/1982 | Testerman |
| 4,378,797 | A | 4/1983 | Osterholm |
| 4,445,500 | A | 5/1984 | Osterholm |
| 4,735,208 | A | 4/1988 | Wyler et al. |
| 4,765,341 | A | 8/1988 | Mower et al. |
| 4,841,973 | A | 6/1989 | Stecker |
| 5,067,495 | A | 11/1991 | Brehm |
| 5,099,846 | A | 3/1992 | Hardy |
| 5,222,494 | A | 6/1993 | Baker, Jr. |
| 5,255,693 | A | 10/1993 | Dutcher |
| 5,259,387 | A | 11/1993 | dePinto |
| 5,304,206 | A | 4/1994 | Baker, Jr. et al. |
| 5,344,438 | A | 9/1994 | Testerman et al. |
| 5,361,763 | A | 11/1994 | Kao et al. |
| 5,452,407 | A | 9/1995 | Crook |
| 5,560,360 | A | 10/1996 | Filler et al. |
| 5,565,949 | A | 10/1996 | Kasha, Jr. |
| 5,593,427 | A | 1/1997 | Gliner et al. |
| 5,601,612 | A | 2/1997 | Gliner et al. |
| 5,607,454 | A | 3/1997 | Cameron et al. |
| 5,620,470 | A | 4/1997 | Gliner et al. |
| 5,651,767 | A | 7/1997 | Schulmann |
| 5,711,316 | A | 1/1998 | Elsberry et al. |
| 5,713,922 | A | 2/1998 | King |
| 5,716,377 | A | 2/1998 | Rise et al. |
| 5,724,985 | A | 3/1998 | Snell et al. |
| 5,749,904 | A | 5/1998 | Gliner et al. |
| 5,749,905 | A | 5/1998 | Gliner et al. |
| 5,776,170 | A | 7/1998 | MacDonald et al. |
| 5,782,762 | A | 7/1998 | Vining |
| 5,792,205 | A | 8/1998 | Alt et al. |
| 5,843,148 | A | 12/1998 | Gijsbers et al. |
| 5,859,922 | A | 1/1999 | Hoffmann |
| 5,868,740 | A | 2/1999 | LeVeen et al. |
| 5,897,583 | A | 4/1999 | Meyer et al. |
| 5,910,804 | A | 6/1999 | Fortenbery et al. |
| 5,925,070 | A | 7/1999 | King et al. |
| 5,938,688 | A | 8/1999 | Schiff |
| 5,938,690 | A | 8/1999 | Law et al. |
| 5,978,713 | A | 11/1999 | Prutchi et al. |
| 6,016,449 | A | 1/2000 | Fischell et al. |
| 6,029,090 | A | 2/2000 | Herbst |
| 6,029,091 | A | 2/2000 | de la Rama et al. |
| 6,050,992 | A | 4/2000 | Nichols |
| 6,058,331 | A | 5/2000 | King |
| 6,066,163 | A | 5/2000 | John |
| 6,080,187 | A | 6/2000 | Alt et al. |
| 6,083,162 | A | 7/2000 | Vining |
| 6,094,598 | A | 7/2000 | Elsberry et al. |
| 6,096,756 | A | 8/2000 | Crain et al. |
| 6,106,460 | A | 8/2000 | Panescu et al. |
| 6,109,269 | A | 8/2000 | Rise et al. |
| 6,128,538 | A | 10/2000 | Fischell et al. |
| 6,129,685 | A | 10/2000 | Howard, III |
| 6,146,390 | A | 11/2000 | Heilbrun et al. |
| 6,161,044 | A | 12/2000 | Silverstone |
| 6,167,311 | A | 12/2000 | Rezai |
| 6,181,969 | B1 | 1/2001 | Gord |
| 6,192,266 | B1 | 2/2001 | Dupree et al. |
| 6,205,361 | B1 | 3/2001 | Kuzma |
| 6,208,881 | B1 | 3/2001 | Champeau |
| 6,240,308 | B1 | 5/2001 | Hardy et al. |
| 6,246,912 | B1 | 6/2001 | Sluijter et al. |
| 6,253,109 | B1 | 6/2001 | Gielen |
| 6,289,239 | B1 | 9/2001 | Panescu et al. |
| 6,301,492 | B1 | 10/2001 | Zonenshayn |
| 6,310,619 | B1 | 10/2001 | Rice |
| 6,319,241 | B1 | 11/2001 | King |
| 6,336,899 | B1 | 1/2002 | Yamazaki |
| 6,343,226 | B1 | 1/2002 | Sunde et al. |
| 6,351,675 | B1 | 2/2002 | Tholen et al. |
| 6,353,762 | B1 | 3/2002 | Baudino et al. |
| 6,366,813 | B1 | 4/2002 | Dilorenzo |
| 6,368,331 | B1 | 4/2002 | Front et al. |
| 6,389,311 | B1 | 5/2002 | Whayne et al. |
| 6,393,325 | B1 | 5/2002 | Mann et al. |
| 6,421,566 | B1 | 7/2002 | Holsheimer |
| 6,435,878 | B1 | 8/2002 | Reynolds et al. |
| 6,442,432 | B2 | 8/2002 | Lee |
| 6,463,328 | B1 | 10/2002 | John |
| 6,491,699 | B1 | 12/2002 | Henderson et al. |
| 6,494,831 | B1 | 12/2002 | Koritzinsky |
| 6,507,759 | B1 | 1/2003 | Prutchi et al. |
| 6,510,347 | B2 | 1/2003 | Borkan |
| 6,516,227 | B1 | 2/2003 | Meadows et al. |
| 6,517,480 | B1 | 2/2003 | Krass |
| 6,539,263 | B1 | 3/2003 | Schiff |
| 6,560,490 | B2 | 5/2003 | Grill et al. |
| 6,579,280 | B1 | 6/2003 | Kovach et al. |
| 6,600,956 | B2 | 7/2003 | Maschino et al. |
| 6,606,523 | B1 | 8/2003 | Jenkins |
| 6,609,029 | B1 | 8/2003 | Mann et al. |
| 6,609,031 | B1 | 8/2003 | Law et al. |
| 6,609,032 | B1 | 8/2003 | Woods et al. |
| 6,622,048 | B1 | 9/2003 | Mann et al. |
| 6,631,297 | B1 | 10/2003 | Mo |
| 6,654,642 | B2 | 11/2003 | North et al. |
| 6,662,053 | B2 | 12/2003 | Borkan |
| 6,675,046 | B2 | 1/2004 | Holsheimer |
| 6,684,106 | B2 | 1/2004 | Herbst |
| 6,687,392 | B1 | 2/2004 | Touzawa et al. |
| 6,690,972 | B2 | 2/2004 | Conley et al. |
| 6,690,974 | B2 | 2/2004 | Archer et al. |
| 6,692,315 | B1 | 2/2004 | Soumillion et al. |
| 6,694,162 | B2 | 2/2004 | Hartlep |
| 6,694,163 | B1 | 2/2004 | Vining |
| 6,708,096 | B1 | 3/2004 | Frei et al. |
| 6,721,603 | B2 | 4/2004 | Zabara et al. |
| 6,741,892 | B1 | 5/2004 | Meadows et al. |
| 6,748,098 | B1 | 6/2004 | Rosenfeld |
| 6,748,276 | B1 | 6/2004 | Daignault, Jr. et al. |
| 6,778,846 | B1 | 8/2004 | Martinez et al. |
| 6,788,969 | B2 | 9/2004 | Dupree et al. |
| 6,795,737 | B2 | 9/2004 | Gielen et al. |
| 6,827,681 | B2 | 12/2004 | Tanner et al. |
| 6,830,544 | B2 | 12/2004 | Tanner |
| 6,845,267 | B2 | 1/2005 | Harrison et al. |
| 6,850,802 | B2 | 2/2005 | Holsheimer |
| 6,895,280 | B2 | 5/2005 | Meadows et al. |
| 6,909,913 | B2 | 6/2005 | Vining |
| 6,937,891 | B2 | 8/2005 | Leinders et al. |
| 6,937,903 | B2 | 8/2005 | Schuler et al. |
| 6,944,497 | B2 | 9/2005 | Stypulkowski |
| 6,944,501 | B1 | 9/2005 | Pless |
| 6,950,707 | B2 | 9/2005 | Whitehurst |
| 6,969,388 | B2 | 11/2005 | Goldman et al. |
| 6,993,384 | B2 | 1/2006 | Bradley et al. |
| 7,003,349 | B1 | 2/2006 | Andersson et al. |

(56)                References Cited

U.S. PATENT DOCUMENTS

| | | | |
|---|---|---|---|
| 7,003,352 B1 | 2/2006 | Whitehurst | |
| 7,008,370 B2 | 3/2006 | Tanner et al. | |
| 7,008,413 B2 | 3/2006 | Kovach et al. | |
| 7,035,690 B2 | 4/2006 | Goetz | |
| 7,043,293 B1 | 5/2006 | Baura | |
| 7,047,082 B1 | 5/2006 | Schrom et al. | |
| 7,047,084 B2 | 5/2006 | Erickson et al. | |
| 7,050,857 B2 | 5/2006 | Samuelsson et al. | |
| 7,054,692 B1 | 5/2006 | Whitehurst et al. | |
| 7,058,446 B2 | 6/2006 | Schuler et al. | |
| 7,082,333 B1 | 7/2006 | Bauhahn et al. | |
| 7,107,102 B2 | 9/2006 | Daignault et al. | |
| 7,126,000 B2 | 10/2006 | Ogawa et al. | |
| 7,127,297 B2 | 10/2006 | Law et al. | |
| 7,136,518 B2 | 11/2006 | Griffin et al. | |
| 7,136,695 B2 | 11/2006 | Pless et al. | |
| 7,142,923 B2 | 11/2006 | North et al. | |
| 7,146,219 B2 | 12/2006 | Sieracki et al. | |
| 7,146,223 B1 | 12/2006 | King | |
| 7,151,961 B1 | 12/2006 | Whitehurst | |
| 7,155,279 B2 | 12/2006 | Whitehurst | |
| 7,167,760 B2 | 1/2007 | Dawant et al. | |
| 7,177,674 B2 | 2/2007 | Echauz et al. | |
| 7,181,286 B2 | 2/2007 | Sieracki et al. | |
| 7,184,837 B2 | 2/2007 | Goetz | |
| 7,191,014 B2 | 3/2007 | Kobayashi et al. | |
| 7,203,548 B2 | 4/2007 | Whitehurst et al. | |
| 7,209,787 B2 | 4/2007 | Dilorenzo | |
| 7,211,050 B1 | 5/2007 | Caplygin | |
| 7,216,000 B2 | 5/2007 | Sieracki et al. | |
| 7,217,276 B2 | 5/2007 | Henderson | |
| 7,218,968 B2 | 5/2007 | Condie et al. | |
| 7,228,179 B2 | 6/2007 | Campen et al. | |
| 7,231,254 B2 | 6/2007 | DiLorenzo | |
| 7,236,830 B2 | 6/2007 | Gliner | |
| 7,239,910 B2 | 7/2007 | Tanner | |
| 7,239,916 B2 | 7/2007 | Thompson et al. | |
| 7,239,926 B2 | 7/2007 | Goetz | |
| 7,242,984 B2 | 7/2007 | DiLorenzo | |
| 7,244,150 B1 | 7/2007 | Brase et al. | |
| 7,252,090 B2 | 8/2007 | Goetz | |
| 7,254,445 B2 | 8/2007 | Law et al. | |
| 7,254,446 B1 | 8/2007 | Erickson | |
| 7,257,447 B2 | 8/2007 | Cates et al. | |
| 7,266,412 B2 | 9/2007 | Stypulkowski | |
| 7,289,761 B2 | 10/2007 | Mazar | |
| 7,294,107 B2 | 11/2007 | Simon et al. | |
| 7,295,876 B1 | 11/2007 | Erickson | |
| 7,299,096 B2 | 11/2007 | Balzer et al. | |
| 7,308,302 B1 | 12/2007 | Schuler et al. | |
| 7,313,430 B2 | 12/2007 | Urquhart | |
| 7,324,851 B1 | 1/2008 | DiLorenzo | |
| 7,346,282 B2 | 3/2008 | Sakanaka et al. | |
| 7,346,382 B2 | 3/2008 | McIntyre et al. | |
| 7,385,443 B1 | 6/2008 | Denison | |
| 7,388,974 B2 | 6/2008 | Yanagita | |
| 7,437,193 B2 | 10/2008 | Parramon et al. | |
| 7,450,997 B1 | 11/2008 | Pianca et al. | |
| 7,454,245 B2 | 11/2008 | Armstrong et al. | |
| 7,463,928 B2 | 12/2008 | Lee et al. | |
| 7,499,048 B2 | 3/2009 | Sieracki et al. | |
| 7,505,815 B2 | 3/2009 | Lee et al. | |
| 7,548,786 B2 | 6/2009 | Lee et al. | |
| 7,565,199 B2 | 7/2009 | Sheffield et al. | |
| 7,596,414 B2 | 9/2009 | Whitehurst et al. | |
| 7,603,177 B2 | 10/2009 | Sieracki et al. | |
| 7,610,103 B2 | 10/2009 | Whitehurst et al. | |
| 7,617,002 B2 | 11/2009 | Goetz | |
| 7,623,918 B2 | 11/2009 | Goetz | |
| 7,650,184 B2 | 1/2010 | Walter | |
| 7,657,319 B2 | 2/2010 | Goetz et al. | |
| 7,672,734 B2 | 3/2010 | Anderson et al. | |
| 7,676,273 B2 | 3/2010 | Goetz et al. | |
| 7,680,526 B2 | 3/2010 | McIntyre et al. | |
| 7,734,340 B2 | 6/2010 | De Ridder | |
| 7,761,165 B1 | 7/2010 | He et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,826,902 B2 | 11/2010 | Stone et al. | |
| 7,848,802 B2 | 12/2010 | Goetz et al. | |
| 7,860,548 B2 | 12/2010 | McIntyre et al. | |
| 7,896,808 B1 | 3/2011 | Koh et al. | |
| 7,904,134 B2 | 3/2011 | McIntyre et al. | |
| 7,945,105 B1 | 5/2011 | Jaenisch | |
| 7,949,395 B2 | 5/2011 | Kuzma | |
| 7,974,706 B2 | 7/2011 | Moffitt et al. | |
| 8,000,794 B2 | 8/2011 | Lozano | |
| 8,019,439 B2 | 9/2011 | Kuzma et al. | |
| 8,019,443 B2 | 9/2011 | Schleicher et al. | |
| 8,175,710 B2 | 5/2012 | He | |
| 8,180,601 B2 | 5/2012 | Butson et al. | |
| 8,187,209 B1 | 5/2012 | Giuffrida | |
| 8,190,250 B2 * | 5/2012 | Moffitt | A61N 1/36185 |
| | | | 607/148 |
| 8,195,300 B2 | 6/2012 | Gliner et al. | |
| 8,209,027 B2 | 6/2012 | Butson et al. | |
| 8,224,450 B2 | 7/2012 | Brase | |
| 8,257,684 B2 | 9/2012 | Covalin et al. | |
| 8,262,714 B2 | 9/2012 | Hulvershorn et al. | |
| 8,271,094 B1 | 9/2012 | Moffitt et al. | |
| 8,280,514 B2 | 10/2012 | Lozano et al. | |
| 8,295,944 B2 | 10/2012 | Howard et al. | |
| 8,306,627 B2 | 11/2012 | Armstrong | |
| 8,326,433 B2 | 12/2012 | Blum et al. | |
| 8,359,107 B2 | 1/2013 | Pianca et al. | |
| 8,364,278 B2 | 1/2013 | Pianca et al. | |
| 8,369,954 B2 | 2/2013 | Stack et al. | |
| 8,379,952 B2 | 2/2013 | McIntyre et al. | |
| 8,391,985 B2 | 3/2013 | McDonald | |
| 8,412,349 B2 | 4/2013 | Barker | |
| 8,429,174 B2 | 4/2013 | Ramani et al. | |
| 8,452,415 B2 | 5/2013 | Goetz et al. | |
| 8,467,883 B2 | 6/2013 | Chen et al. | |
| 8,473,061 B2 | 6/2013 | Moffitt et al. | |
| 8,483,237 B2 | 7/2013 | Zimmermann et al. | |
| 8,543,189 B2 | 9/2013 | Paitel et al. | |
| 8,571,665 B2 | 10/2013 | Moffitt et al. | |
| 8,589,316 B2 | 11/2013 | Lujan et al. | |
| 8,594,800 B2 | 11/2013 | Butson et al. | |
| 8,594,801 B2 | 11/2013 | Corndorf et al. | |
| 8,606,360 B2 | 12/2013 | Butson et al. | |
| 8,620,452 B2 | 12/2013 | King et al. | |
| 8,649,845 B2 | 2/2014 | McIntyre et al. | |
| 8,675,945 B2 | 3/2014 | Barnhorst et al. | |
| 8,679,038 B1 | 3/2014 | Giuffrida | |
| 8,688,235 B1 | 4/2014 | Pianca et al. | |
| 8,744,596 B2 | 6/2014 | Howard | |
| 8,751,008 B2 | 6/2014 | Carlton et al. | |
| 8,751,016 B2 | 6/2014 | Schleicher et al. | |
| 8,774,941 B2 | 7/2014 | Pianca | |
| 8,792,993 B2 | 7/2014 | Pianca et al. | |
| 8,831,731 B2 | 9/2014 | Blum et al. | |
| 8,831,742 B2 | 9/2014 | Pianca et al. | |
| 8,845,557 B1 | 9/2014 | Giuffrida et al. | |
| 8,849,632 B2 | 9/2014 | Sparks et al. | |
| 8,855,773 B2 | 10/2014 | Kokones et al. | |
| 8,868,199 B2 | 10/2014 | Kaula et al. | |
| 8,913,804 B2 | 12/2014 | Blum et al. | |
| 8,918,183 B2 | 12/2014 | Carlton et al. | |
| 8,918,184 B1 | 12/2014 | Torgerson et al. | |
| 8,923,976 B2 | 12/2014 | Johanek et al. | |
| 8,936,622 B2 | 1/2015 | Wales et al. | |
| 8,958,615 B2 | 2/2015 | Blum et al. | |
| 8,972,023 B2 | 3/2015 | Bradley et al. | |
| 8,986,382 B2 | 3/2015 | Bentley et al. | |
| 9,020,789 B2 | 4/2015 | Butson et al. | |
| 9,026,317 B2 | 5/2015 | Furukawa et al. | |
| 9,039,740 B2 | 5/2015 | Wales et al. | |
| 9,050,470 B2 | 6/2015 | Carlton et al. | |
| 9,061,138 B2 | 6/2015 | Pianca | |
| 9,072,905 B2 | 7/2015 | Kokones et al. | |
| 9,081,488 B2 | 7/2015 | Soederstroem | |
| 9,084,896 B2 | 7/2015 | Kokones et al. | |

(56)                    References Cited

U.S. PATENT DOCUMENTS

| | | | |
|---|---|---|---|
| 9,135,400 | B2 | 9/2015 | McIntyre et al. |
| 9,149,630 | B2 | 10/2015 | Howard et al. |
| 9,162,056 | B2 | 10/2015 | Pianca |
| 9,220,889 | B2 | 12/2015 | Carlton et al. |
| 9,227,074 | B2 | 1/2016 | Carcieri et al. |
| 9,235,685 | B2 | 1/2016 | McIntyre et al. |
| 9,248,272 | B2 | 2/2016 | Romero |
| 9,248,296 | B2 | 2/2016 | Carcieri et al. |
| 9,254,387 | B2 | 2/2016 | Blum et al. |
| 9,272,153 | B2 | 3/2016 | Blum et al. |
| 9,289,596 | B2 | 3/2016 | Leven |
| 9,289,600 | B2 | 3/2016 | Govea et al. |
| 9,302,110 | B2 | 4/2016 | Kokones et al. |
| 9,308,372 | B2 | 4/2016 | Sparks et al. |
| 9,310,985 | B2 | 4/2016 | Blum et al. |
| 9,327,111 | B2 | 5/2016 | Pianca et al. |
| 9,358,398 | B2 | 6/2016 | Moffitt et al. |
| 9,364,665 | B2 | 6/2016 | Bokil et al. |
| 9,381,348 | B2 | 7/2016 | Romero et al. |
| 9,387,325 | B1 | 7/2016 | Min et al. |
| 9,415,154 | B2 | 8/2016 | Leven |
| 9,474,903 | B2 | 10/2016 | Chen et al. |
| 9,492,655 | B2 | 11/2016 | Pianca et al. |
| 9,498,620 | B2 | 11/2016 | Romero et al. |
| 9,526,902 | B2 | 12/2016 | Blum et al. |
| 9,533,141 | B2 | 1/2017 | Black et al. |
| 9,566,596 | B2 | 2/2017 | Kim et al. |
| 9,572,982 | B2 | 2/2017 | Burnes et al. |
| 9,586,053 | B2 | 3/2017 | Moffitt et al. |
| 9,592,389 | B2 | 3/2017 | Moffitt |
| 9,610,435 | B2 | 4/2017 | Schleicher et al. |
| 9,636,498 | B2 | 5/2017 | Leven |
| 9,649,489 | B2 | 5/2017 | Wechter et al. |
| 9,669,210 | B2 | 6/2017 | Barker et al. |
| 9,713,720 | B2 | 7/2017 | Zhu |
| 9,775,988 | B2 | 10/2017 | Govea et al. |
| 9,792,412 | B2 | 10/2017 | Moffitt et al. |
| 9,821,167 | B2 | 11/2017 | Carcieri et al. |
| 9,887,470 | B2 | 2/2018 | Nguyen-Stella et al. |
| 9,925,382 | B2 | 3/2018 | Carlton et al. |
| 9,959,940 | B2 | 5/2018 | Moffitt et al. |
| 9,974,959 | B2 | 5/2018 | Moffitt et al. |
| 9,987,482 | B2 | 6/2018 | Nageri et al. |
| 10,067,659 | B2 | 9/2018 | Bokil |
| 10,071,242 | B2 | 9/2018 | Leven |
| 10,071,249 | B2 | 9/2018 | Zottola |
| 10,086,202 | B2 | 10/2018 | Seim et al. |
| 10,086,205 | B2 | 10/2018 | Grill et al. |
| 10,213,148 | B2 | 2/2019 | Min et al. |
| 10,226,616 | B2 | 3/2019 | Barker |
| 10,265,528 | B2 | 4/2019 | Carcieri et al. |
| 10,265,531 | B2 | 4/2019 | Bokil |
| 10,286,205 | B2 | 5/2019 | Steinke et al. |
| 10,300,282 | B2 | 5/2019 | Torgerson et al. |
| 10,335,607 | B2 | 7/2019 | Orinski |
| 10,357,657 | B2 | 7/2019 | Moffitt et al. |
| 10,369,364 | B2 | 8/2019 | Moffitt et al. |
| 10,406,353 | B2 | 9/2019 | Wechter |
| 10,485,969 | B2 | 11/2019 | Govea et al. |
| 10,493,269 | B2 | 12/2019 | Stoffregen et al. |
| 10,525,257 | B2 | 1/2020 | Govea et al. |
| 10,525,266 | B2 | 1/2020 | Moffitt et al. |
| 10,603,498 | B2 | 3/2020 | Blum et al. |
| 10,625,072 | B2 | 4/2020 | Serrano Carmona |
| 10,631,937 | B2 | 4/2020 | Tyulmankov et al. |
| 10,639,488 | B2 | 5/2020 | Kalgren et al. |
| 10,653,330 | B2 | 5/2020 | Angle et al. |
| 10,675,468 | B2 | 6/2020 | Torgerson |
| 10,709,886 | B2 | 7/2020 | Nagaoka et al. |
| 10,709,888 | B2 | 7/2020 | Pianca |
| 10,716,505 | B2 | 7/2020 | Blum et al. |
| 10,780,282 | B2 | 9/2020 | Mustakos et al. |
| 10,814,127 | B2 | 10/2020 | Nageri et al. |
| 10,814,140 | B2 | 10/2020 | Zhang et al. |
| 10,835,739 | B2 | 11/2020 | Sandhu |
| 10,850,101 | B2 | 12/2020 | Zhang et al. |
| 10,857,351 | B2 | 12/2020 | Wang et al. |
| 10,960,203 | B2 | 3/2021 | Tyler et al. |
| 11,020,052 | B2 | 6/2021 | Zuckerman-Stark et al. |
| 11,285,329 | B2 | 3/2022 | Carcieri et al. |
| 11,298,550 | B2 | 4/2022 | Howard et al. |
| 11,357,986 | B2 | 6/2022 | Steinke et al. |
| 11,517,755 | B2 | 12/2022 | Zhang et al. |
| 11,529,510 | B2 | 12/2022 | Leven |
| 11,707,622 | B2 | 7/2023 | Juarez Paz et al. |
| 11,745,010 | B2 | 9/2023 | Donega et al. |
| 2001/0031071 | A1 | 10/2001 | Nichols et al. |
| 2002/0032375 | A1 | 3/2002 | Bauch et al. |
| 2002/0062143 | A1 | 5/2002 | Baudino et al. |
| 2002/0087201 | A1 | 7/2002 | Firlik et al. |
| 2002/0099295 | A1 | 7/2002 | Gil et al. |
| 2002/0115603 | A1 | 8/2002 | Whitehouse |
| 2002/0116030 | A1 | 8/2002 | Rezei |
| 2002/0123780 | A1 | 9/2002 | Grill et al. |
| 2002/0128694 | A1 | 9/2002 | Holsheimer |
| 2002/0151939 | A1 | 10/2002 | Rezai |
| 2002/0183607 | A1 | 12/2002 | Bauch et al. |
| 2002/0183740 | A1 | 12/2002 | Edwards et al. |
| 2002/0183817 | A1 | 12/2002 | Van Venrooij et al. |
| 2003/0097159 | A1 | 5/2003 | Schiff et al. |
| 2003/0149450 | A1 | 8/2003 | Mayberg |
| 2003/0171791 | A1 | 9/2003 | KenKnight et al. |
| 2003/0212439 | A1 | 11/2003 | Schuler et al. |
| 2004/0034394 | A1 | 2/2004 | Woods et al. |
| 2004/0044279 | A1 | 3/2004 | Lewin et al. |
| 2004/0044378 | A1 | 3/2004 | Holsheimer |
| 2004/0044379 | A1 | 3/2004 | Holsheimer |
| 2004/0054297 | A1 | 3/2004 | Wingeier et al. |
| 2004/0059395 | A1 | 3/2004 | North et al. |
| 2004/0106916 | A1 | 6/2004 | Quaid et al. |
| 2004/0133248 | A1 | 7/2004 | Frei et al. |
| 2004/0152957 | A1 | 8/2004 | Stivoric et al. |
| 2004/0181262 | A1 | 9/2004 | Bauhahn |
| 2004/0186532 | A1 | 9/2004 | Tadlock |
| 2004/0193231 | A1 | 9/2004 | David et al. |
| 2004/0199216 | A1 | 10/2004 | Lee et al. |
| 2004/0267330 | A1 | 12/2004 | Lee et al. |
| 2005/0021090 | A1 | 1/2005 | Schuler et al. |
| 2005/0033380 | A1 | 2/2005 | Tanner et al. |
| 2005/0049649 | A1 | 3/2005 | Luders et al. |
| 2005/0060001 | A1 | 3/2005 | Singhal et al. |
| 2005/0060009 | A1 | 3/2005 | Goetz |
| 2005/0070781 | A1 | 3/2005 | Dawant et al. |
| 2005/0075689 | A1 | 4/2005 | Toy et al. |
| 2005/0085714 | A1 | 4/2005 | Foley et al. |
| 2005/0113885 | A1 | 5/2005 | Haubrich et al. |
| 2005/0165294 | A1 | 7/2005 | Weiss |
| 2005/0171587 | A1 | 8/2005 | Daglow et al. |
| 2005/0228250 | A1 | 10/2005 | Bitter et al. |
| 2005/0251061 | A1 | 11/2005 | Schuler et al. |
| 2005/0261061 | A1 | 11/2005 | Nguyen et al. |
| 2005/0261601 | A1 | 11/2005 | Schuler et al. |
| 2005/0261747 | A1 | 11/2005 | Schuler et al. |
| 2005/0267347 | A1 | 12/2005 | Oster |
| 2005/0288732 | A1 | 12/2005 | Schuler et al. |
| 2006/0004422 | A1 | 1/2006 | De Ridder |
| 2006/0017749 | A1 | 1/2006 | McIntyre et al. |
| 2006/0020292 | A1 | 1/2006 | Goetz et al. |
| 2006/0069415 | A1 | 3/2006 | Cameron et al. |
| 2006/0094951 | A1 | 5/2006 | Dean et al. |
| 2006/0095088 | A1 | 5/2006 | De Riddler |
| 2006/0155340 | A1 | 7/2006 | Schuler et al. |
| 2006/0173496 | A1 | 8/2006 | Lombardi et al. |
| 2006/0206169 | A1 | 9/2006 | Schuler |
| 2006/0218007 | A1 | 9/2006 | Bjorner et al. |
| 2006/0224189 | A1 | 10/2006 | Schuler et al. |
| 2006/0235472 | A1 | 10/2006 | Goetz et al. |
| 2006/0259079 | A1 | 11/2006 | King |
| 2006/0259099 | A1 | 11/2006 | Goetz et al. |
| 2007/0000372 | A1 | 1/2007 | Rezai et al. |
| 2007/0017749 | A1 | 1/2007 | Dold et al. |
| 2007/0027499 | A1 | 2/2007 | Maschino et al. |
| 2007/0027514 | A1 | 2/2007 | Gerber |
| 2007/0043268 | A1 | 2/2007 | Russell |

(56)  References Cited

U.S. PATENT DOCUMENTS

| | | |
|---|---|---|
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150026 A1 | 6/2007 | Bourget et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0179557 A1 | 8/2007 | Maschino et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0260283 A1 | 11/2007 | Li |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0046037 A1 | 2/2008 | Haubrich et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0091248 A1 | 4/2008 | Libbus et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215101 A1 | 9/2008 | Rezai et al. |
| 2008/0215118 A1 | 9/2008 | Goetz et al. |
| 2008/0227139 A1 | 9/2008 | Deisseroth et al. |
| 2008/0238749 A1 | 10/2008 | Corndorf |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054947 A1 | 2/2009 | Bourn et al. |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0163975 A1 | 6/2009 | Gerber et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0228073 A1 | 9/2009 | Scholten |
| 2009/0242399 A1 | 10/2009 | Kamath et al. |
| 2009/0270949 A1 | 10/2009 | Kalpin et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010387 A1 | 1/2010 | Skelton et al. |
| 2010/0010432 A1 | 1/2010 | Skelton |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0057161 A1 | 3/2010 | Machado et al. |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0152807 A1 | 6/2010 | Grill et al. |
| 2010/0179562 A1 | 7/2010 | Linker et al. |
| 2010/0211135 A1 | 8/2010 | Caparso et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0054559 A1 | 3/2011 | Rosenberg et al. |
| 2011/0066407 A1 | 3/2011 | Butson et al. |
| 2011/0078900 A1 | 4/2011 | Pianca et al. |
| 2011/0093045 A1 | 4/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0137372 A1 | 6/2011 | Makous et al. |
| 2011/0160796 A1 | 6/2011 | Lane et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0224665 A1 | 9/2011 | Crosby et al. |
| 2011/0224680 A1 | 9/2011 | Barker |
| 2011/0238129 A1 | 9/2011 | Moffitt |
| 2011/0251583 A1 | 10/2011 | Miyazawa et al. |
| 2011/0270348 A1 | 11/2011 | Goetz |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313485 A1 | 12/2011 | DeMulling et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |

(56) References Cited

U.S. PATENT DOCUMENTS

| | | |
|---|---|---|
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0239109 A1 | 9/2012 | Lee |
| 2012/0239115 A1 | 9/2012 | Lee |
| 2012/0265103 A1 | 10/2012 | Policker et al. |
| 2012/0265262 A1 | 10/2012 | Osorio |
| 2012/0265268 A1 | 10/2012 | Blum et al. |
| 2012/0271189 A1 | 10/2012 | Nelson et al. |
| 2012/0277833 A1 | 11/2012 | Gerber et al. |
| 2012/0302912 A1 | 11/2012 | Moffitt et al. |
| 2012/0303087 A1 | 11/2012 | Moffitt et al. |
| 2012/0303098 A1 | 11/2012 | Perryman |
| 2012/0314919 A1 | 12/2012 | Sparks et al. |
| 2012/0314924 A1 | 12/2012 | Carlton et al. |
| 2012/0316615 A1 | 12/2012 | Digiore et al. |
| 2012/0316619 A1 | 12/2012 | Goetz et al. |
| 2012/0330374 A1 | 12/2012 | Blum et al. |
| 2012/0330622 A1 | 12/2012 | Butson et al. |
| 2013/0035740 A1 | 2/2013 | Sharma et al. |
| 2013/0039550 A1 | 2/2013 | Blum et al. |
| 2013/0053926 A1 | 2/2013 | Hincapie Ordonez et al. |
| 2013/0060301 A1 | 3/2013 | Polefko et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0226261 A1 | 8/2013 | Sparks et al. |
| 2013/0245722 A1 | 9/2013 | Ternes et al. |
| 2013/0261684 A1 | 10/2013 | Howard |
| 2013/0289380 A1 | 10/2013 | Molnar et al. |
| 2013/0289660 A1 | 10/2013 | Molnar et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039586 A1 | 2/2014 | Barker et al. |
| 2014/0039587 A1 | 2/2014 | Romero |
| 2014/0063017 A1 | 3/2014 | Kaula et al. |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0074180 A1 | 3/2014 | Heldman et al. |
| 2014/0081366 A1 | 3/2014 | Bentley et al. |
| 2014/0107731 A1 | 4/2014 | Stone et al. |
| 2014/0122379 A1 | 5/2014 | Moffitt et al. |
| 2014/0200633 A1 | 7/2014 | Moffitt |
| 2014/0243926 A1 | 8/2014 | Carcieri |
| 2014/0276707 A1 | 9/2014 | Jaax |
| 2014/0276927 A1 | 9/2014 | Barker |
| 2014/0277282 A1 | 9/2014 | Jaax |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0073431 A1 | 3/2015 | Barker |
| 2015/0073432 A1 | 3/2015 | Barker |
| 2015/0134031 A1 | 5/2015 | Moffitt et al. |
| 2015/0151113 A1 | 6/2015 | Govea et al. |
| 2015/0246231 A1 | 9/2015 | Martens et al. |
| 2015/0360039 A1 | 12/2015 | Lempka et al. |
| 2016/0001087 A1 | 1/2016 | Moffitt |
| 2016/0008632 A1 | 1/2016 | Wetmore et al. |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0030750 A1 | 2/2016 | Bokil et al. |
| 2016/0045748 A1 | 2/2016 | Astrom et al. |
| 2016/0082252 A1 | 3/2016 | Hershey et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0144186 A1 | 5/2016 | Kaemmerer et al. |
| 2016/0175594 A1 | 6/2016 | Min et al. |
| 2016/0206380 A1 | 7/2016 | Sparks et al. |
| 2016/0228692 A1 | 8/2016 | Steinke et al. |
| 2016/0256691 A1 | 9/2016 | Cecchi et al. |
| 2016/0256693 A1 | 9/2016 | Parramon |
| 2016/0317800 A1 | 11/2016 | Barker |
| 2016/0346557 A1 | 12/2016 | Bokil |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0100601 A1 | 4/2017 | Xiao et al. |
| 2017/0106197 A1 | 4/2017 | Wechter et al. |
| 2017/0197086 A1 | 7/2017 | Howard et al. |
| 2017/0225007 A1 | 8/2017 | Orinski |
| 2017/0252570 A1 | 9/2017 | Serrano Carmona et al. |
| 2017/0259078 A1 | 9/2017 | Howard |
| 2017/0304610 A1 | 10/2017 | Huibregtse et al. |
| 2017/0304633 A1 | 10/2017 | Zhang |
| 2017/0333692 A1 | 11/2017 | Stoffregen et al. |
| 2017/0372039 A1 | 12/2017 | Mustakos et al. |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0104500 A1 | 4/2018 | Blum et al. |
| 2018/0110971 A1 | 4/2018 | Serrano Carmona |
| 2018/0133481 A1 | 5/2018 | Von Zitzewitz et al. |
| 2018/0185650 A1 | 7/2018 | Shah |
| 2018/0193655 A1 | 7/2018 | Zhang et al. |
| 2018/0214700 A1 | 8/2018 | Vansickle et al. |
| 2018/0264278 A1 | 9/2018 | Laghi |
| 2018/0272142 A1 | 9/2018 | Zhang et al. |
| 2018/0280698 A1 | 10/2018 | Steinke et al. |
| 2018/0296828 A1 | 10/2018 | Bradley et al. |
| 2018/0333173 A1 | 11/2018 | Wang |
| 2018/0333587 A1* | 11/2018 | Howard ............... A61B 5/0006 |
| 2018/0369589 A1 | 12/2018 | Schouenborg |
| 2018/0369606 A1 | 12/2018 | Zhang et al. |
| 2018/0369607 A1 | 12/2018 | Zhang et al. |
| 2019/0015660 A1 | 1/2019 | Zhang et al. |
| 2019/0105503 A1 | 4/2019 | Leven |
| 2019/0184171 A1 | 6/2019 | Mustakos et al. |
| 2019/0209834 A1 | 7/2019 | Zhang et al. |
| 2019/0209849 A1 | 7/2019 | Hershey et al. |
| 2019/0262609 A1 | 8/2019 | Brill et al. |
| 2019/0275331 A1 | 9/2019 | Zhu |
| 2019/0329047 A1 | 10/2019 | Moffitt et al. |
| 2019/0329049 A1 | 10/2019 | Carcieri et al. |
| 2020/0094047 A1 | 3/2020 | Govea et al. |
| 2020/0139127 A1 | 5/2020 | Zhang et al. |
| 2020/0155854 A1 | 5/2020 | Leven et al. |
| 2020/0155859 A1 | 5/2020 | Blum et al. |
| 2020/0171298 A1 | 6/2020 | Goetz et al. |

(56) References Cited

U.S. PATENT DOCUMENTS

| | | | |
|---|---|---|---|
| 2020/0171310 A1 | 6/2020 | Walter et al. | |
| 2020/0179600 A1 | 6/2020 | Zanos et al. | |
| 2020/0179701 A1 | 6/2020 | Pronovici et al. | |
| 2020/0215330 A1 | 7/2020 | Huertas Fernandez et al. | |
| 2020/0222704 A1 | 7/2020 | Moffitt et al. | |
| 2020/0269053 A1 | 8/2020 | Park | |
| 2020/0353254 A1 | 11/2020 | O Laighin et al. | |
| 2020/0376262 A1 | 12/2020 | Clark et al. | |
| 2020/0376263 A1 | 12/2020 | Zhu | |
| 2020/0398057 A1 | 12/2020 | Esteller et al. | |
| 2021/0008388 A1 | 1/2021 | Vansickle et al. | |
| 2021/0008389 A1 | 1/2021 | Featherstone et al. | |
| 2021/0016111 A1 | 1/2021 | Vansickle et al. | |
| 2021/0023374 A1 | 1/2021 | Block et al. | |
| 2021/0052893 A1 | 2/2021 | Suri et al. | |
| 2021/0113844 A1 | 4/2021 | Zhang et al. | |
| 2021/0128920 A1 | 5/2021 | Grill et al. | |
| 2021/0196956 A1 | 7/2021 | Juárez Paz | |
| 2021/0196964 A1 | 7/2021 | Schnell et al. | |
| 2021/0205613 A1 | 7/2021 | Bradley et al. | |
| 2021/0268268 A1 | 9/2021 | Horn et al. | |
| 2021/0275820 A1 | 9/2021 | Grill, Jr. et al. | |
| 2021/0387002 A1 | 12/2021 | Bourget et al. | |
| 2022/0007980 A1 | 1/2022 | Single | |
| 2022/0008729 A1 | 1/2022 | Zhu | |
| 2022/0040485 A1 | 2/2022 | Li et al. | |
| 2022/0062640 A1 | 3/2022 | Raike et al. | |
| 2022/0072329 A1 | 3/2022 | Howard | |
| 2022/0111213 A1 | 4/2022 | Cassar et al. | |
| 2022/0126100 A1 | 4/2022 | Jackson et al. | |
| 2022/0226641 A1 | 7/2022 | Subramanian | |
| 2022/0257950 A1 | 8/2022 | Moore et al. | |
| 2022/0266026 A1 | 8/2022 | Case et al. | |
| 2022/0296892 A1 | 9/2022 | Esteller et al. | |
| 2022/0296893 A1 | 9/2022 | Steinke et al. | |
| 2022/0339448 A1 | 10/2022 | Jayakumar et al. | |
| 2022/0347479 A1 | 11/2022 | Esteller et al. | |
| 2022/0355114 A1 | 11/2022 | Moore et al. | |
| 2022/0355115 A1 | 11/2022 | Moore et al. | |
| 2022/0370793 A1 | 11/2022 | Foster et al. | |
| 2022/0370808 A1 | 11/2022 | Esteller | |
| 2022/0387785 A1 | 12/2022 | Huynh et al. | |
| 2022/0395690 A1 | 12/2022 | Haddock et al. | |
| 2023/0048571 A1 | 2/2023 | Poltorak | |
| 2023/0064552 A1 | 3/2023 | Moffitt | |
| 2023/0141183 A1 | 5/2023 | Moore et al. | |
| 2023/0181089 A1 | 6/2023 | Zhang et al. | |
| 2023/0181090 A1 | 6/2023 | Juarez Paz | |
| 2023/0181906 A1 | 6/2023 | Moore et al. | |
| 2023/0248977 A1 | 8/2023 | Esteller et al. | |
| 2023/0264025 A1 | 8/2023 | Malekmohammadi et al. | |
| 2023/0271015 A1 | 8/2023 | Malekmohammadi et al. | |
| 2023/0277849 A1 | 9/2023 | Moffitt et al. | |
| 2023/0277854 A1 | 9/2023 | Gaviao Kilmar | |
| 2024/0058611 A1 | 2/2024 | Steinke et al. | |
| 2024/0065620 A1 | 2/2024 | Moore et al. | |
| 2024/0157151 A1 | 5/2024 | Juarez Paz | |
| 2024/0198110 A1 | 6/2024 | Moore | |
| 2024/0316346 A1 | 9/2024 | Shah et al. | |
| 2024/0359015 A1 | 10/2024 | Steinke et al. | |
| 2025/0010079 A1 | 1/2025 | Bokil | |
| 2025/0050107 A1 | 2/2025 | Moore et al. | |
| 2025/0099749 A1 | 3/2025 | Moffitt et al. | |
| 2025/0249236 A1 | 8/2025 | Nageri et al. | |
| 2025/0249251 A1 | 8/2025 | Gu et al. | |

FOREIGN PATENT DOCUMENTS

| | | | |
|---|---|---|---|
| EP | 1166819 | 1/2002 | |
| EP | 1372780 | 1/2004 | |
| EP | 1559369 | 8/2005 | |
| WO | 97/39797 | 10/1997 | |
| WO | 98/48880 | 11/1998 | |
| WO | 01/90876 | 11/2001 | |
| WO | 02/26314 | 4/2002 | |
| WO | 02/28473 | 4/2002 | |
| WO | 02/065896 | 8/2002 | |
| WO | 02/072192 | 9/2002 | |
| WO | 03/086185 | 10/2003 | |
| WO | 2004/019799 A2 | 3/2004 | |
| WO | 2004041080 | 5/2005 | |
| WO | 2006017053 | 2/2006 | |
| WO | 2006113305 | 10/2006 | |
| WO | 20071097859 | 8/2007 | |
| WO | 20071097861 A1 | 8/2007 | |
| WO | 2007/100427 | 9/2007 | |
| WO | 2007/100428 | 9/2007 | |
| WO | 2007/112061 | 10/2007 | |
| WO | 2009097224 | 8/2009 | |
| WO | WO-2009134476 A1 * | 11/2009 | ............ G16H 40/63 |
| WO | 2010/120823 A2 | 10/2010 | |
| WO | 2011025865 | 3/2011 | |
| WO | 2011/139779 A1 | 11/2011 | |
| WO | 2011/159688 A2 | 12/2011 | |
| WO | 2012088482 | 6/2012 | |
| WO | 2016/025913 | 2/2016 | |
| WO | 2016081099 | 5/2016 | |
| WO | 2016112398 | 7/2016 | |
| WO | 2010/109448 | 9/2020 | |

OTHER PUBLICATIONS

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E., et al., "Computational Intelligence for target assesment in Parkinson's disease," Proceedings of SPIE vol. 4479, Applications and Science of Neural Networks, Fuzzy Systems, and Evolutionary Computation IV (2001), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59(5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys., 29(4) (Dec. 1967), pp. 657-664.

(56) References Cited

OTHER PUBLICATIONS

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

Si. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001 ), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Wakana, S., et al., "Fiber tract-based atlas of human white matter anatomy," Radiology, 230(1) (Jan. 2004), pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.

Yianni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantable Microstimulators" ICM '98 Proceedings of the Tenth International Conference, pp. 67-70.

Butson, Christopher R., et al., "Patient-specific analysis of the volume of tissue activated during deep brain stimulation", NeuroImage. vol. 34. (2007),661-670.

Adler, DE., et al., "The tentorial notch: anatomical variation, morphometric analysis, and classification in 100 human autopsy cases," J. Neurosurg., 96(6), (Jun. 2002), pp. 1103-1112.

Jones et al., "An Advanced Demultiplexing System for Physiological Stimulation", IEEE Transactions on Biomedical Engineering, vol. 44 No. 12 Dec. 1997, pp. 1210-1220.

Mitra PP, Pesaran B. Analysis of dynamic brain imaging data. Biophys J. Feb. 1999;76(2):691-708. doi: 10.1016/S0006-3495(99)77236-X. PMID: 9929474; PMCID: PMC1300074.

Hammer N, Glätzner J, Feja C, Kühne C, Meixensberger J, et al. (2015) Human Vagus Nerve Branching in the Cervical Region. PLOS ONE 10(2): e0118006. Published: Feb. 13, 2015. https://doi.org/10.1371/journal.pone.0118006.

Benoit M. Dawant et al: "The VU-DBS project: integrated and computer-assisted planning, intra-operative placement, and post-operative programming of deep-brain stimulators", Proceedings of SPIE, vol. 6509, Mar. 6, 2007 (Mar. 6, 2007), 11 pages.

Trost M, Su S, Su P, Yen RF, Tseng HM, Barnes A, Ma Y, Eidelberg D. Network modulation by the subthalamic nucleus in the treatment of Parkinson's disease. Neuroimage. May 15, 2006;31(1):301-7. doi: 10.1016/j. neuroimage.2005.12.024. Epub Feb. 8, 2006.

"C.R. Butson, J. Hall, J. Henderson, C. McIntyre. Patient-Specific Models of Deep Brain Stimulation: 3D Visualization of Anatomy, Electrode and Volume of Activation as Afunction of Stimulation Parameters Program No. 1011.11. 2004 Abstract. Washington, DC: Society for Neuroscience, 2004. Online."

Zhang, Y., et al., "Atlas-guided tract reconstruction for automated and comprehensive examination of the white matter anatomy," Neuroimage 52(4) (2010), pp. 1289-1301.

""BioPSE" The Biomedical Problem Solving Environment", htt12://www.sci.utah.edu/cibc/software/index.html, MCRR Center for Integrative Biomedical Computing, (2004).

Andrews, R. J., "Neuroprotection trek—the next generation: neuromodulation I. Techniques-deep brain stimulation, vagus nerve stimulation, and transcranial magnetic stimulation.", Ann NY Acad Sci. 993. (May 2003), 1-13.

(56)                     References Cited

OTHER PUBLICATIONS

Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, Md., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular field potentials and the frequency-filtering properties of extracellular space", Biophys J .. 86(3). (Mar. 2004), 1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.

Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention—Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aflerpotentials on the recovery cycle," J Neurophysiol, 87(2) (Feb. 2002), pp. 995-1006.

(56)         References Cited

OTHER PUBLICATIONS

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Nowinski, W. L., et al., "Statistical analysis of 168 bilateral subthalamic nucleus implantations by means of the probabilistic functional atlas.", Neurosurgery 57(4 Suppl) (Oct. 2005),319-30.

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Butson et al.. "Current Steering to control the volume of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

Mcintyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in Improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45(6). (Jun. 1998),766-772.

Rose, T. L., et al., "Electrical stimulation with Pt electrodes. VIII. Electrochemically safe charge injection limits with 0.2ms pulses

[neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl.. 191, (Sep. 2003), 14-9.

Schwan, H.P., et al., "The conductivity of living tissues.", Ann NY Acad Sci., 65(6). (Aug. 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Geddes, L. A., et al., "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments—electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Izad, Oliver, "Computationally Efficient Method in Predicating Axonal Excitation," Dissertation for Master Degree, Department of Biomedical Engineering, Case Western Reserve University, May 2009.

Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi: 10.1007/BF01908075.

Cover, T.M. et al., "Elements of information theory," (1991) John Wiley & Sons, New York, NY.

Meila, Marina, "Comparing Clusterings by the Variation of Information," Learning Theory and Kernel Machines (2003): 173-187.

Viola, P., et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Indroduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al. "Sketching and Composing Widgets for 3D Manipulation," Eurographics, Apr. 2008, vol. 27, No. 2, pp. 301-310.

Volkmann, J. , et al., "Basic algorithms for the programming of deep brain stimulation in Parkinson's disease", Mov Disord., 21 Suppl 14. (Jun. 2006),S284-9.

Walter, B. L., et al., "Surgical treatment for Parkinson's disease", Lancet Neural. 3(12). (Dec. 2004),719-28.

Wei, X. F., et al., "Current density distributions, field distributions and impedance analysis of segmented deep brain stimulation electrodes", J Neural Eng .. 2(4). (Dec. 2005), 139-47.

US 12,594,424 B2

Page 11

(56)          References Cited

OTHER PUBLICATIONS

Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:447-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.

Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.
An, et al., "Prefrontal cortical projections to longitudinal columns in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T., et al., "Connectional networks within the orbital and medial prefrontal cortex of macaque monkeys," J Comp Neural 371 (2) (1996), pp. 179-207.
Croxson, et al., "Quantitative investigation of connections of the prefrontal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The Neuron simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.

(56)          References Cited

OTHER PUBLICATIONS

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.

Machado. et al., "Functional topography of the ventral striatum and anterior limb of the internal capsule determined by electrical stimulation of awake patients," Clin Neurophysiol 120 (11) (2009), pp. 1941-1948..

Malone, et al., "Deep brain stimulation of the ventral capsule/ventral striatum for treatment-resistant depression," Biol Psychiatry 65 (4) (2009), pp. 267-275.

Mayberg, H. S., et al., "Deep brain stimulation for treatment-resistant depression," Neuron, 45(5) (Mar. 3, 2005), pp. 651-660.

Mayberg, H. S., et al., "Limbic-cortical dysregulation: a proposed model of depression," J Neuropsychiatry Clin Neurosci. 9 (3) (1997), pp. 471-481.

McIntyre, C. C., et al., "Network perspectives on the mechanisms of deep brain stimulation," Neurobiol Dis 38 (3) (2010), pp. 329-337.

Miocinovic, S., et al., "Experimental and theoretical characterization of the voltage distribution generated by deep brain stimulation," Exp Neurol 216 (i) (2009), pp. 166-176.

Nuttin, et al., "Electrical stimulation in anterior limbs of internal capsules in patients with obsessive-compulsive disorder," Lancet 354 (9189) (1999), p. 1526.

Saxena, et al., "Cerebral glucose metabolism in obsessive-compulsive hoarding," Am J Psychiatry. 161 (6) (2004), pp. 1038-1048.

Viola, et al., "Importance-driven focus of attention," IEEE Trans Vis Comput Graph 12 (5) (2006), pp. 933-940.

Wakana, S., et al., "Reproducibility of quantitative tractography methods applied to cerebral white matter," Neuroimage 36 (3) (2007), pp. 630-644.

Mayr et al., "Basic Design and Construction of the Vienna FES Implants: Existing Solutions and Prospects for New Generations of Implants", Medical Engineering & Physics, 2001; 23:53-60.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic implications," Movement Disorders, 17(5), (Sep./Oct. 2002), pp. 969-983.

Bammer, R, et al., "Diffusion tensor imaging using single-shot SENSE-EPI", Magn Reson Med., 48(1 ), (Jul. 2002), pp. 128-136.

Basser, P J., et al., "MR diffusion tensor spectroscopy and imaging," Biophys J., 66(1 ), (Jan. 1994), pp. 259-267.

Basser, P J., et al., "New currents in electrical stimulation of excitable tissues," Annu Rev Biomed Eng., 2, (2000), pp. 377-397.

Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.

Benabid, A L., et al., "Long-term suppression of tremor by chronic stimulation of the ventral intermediate thalamic nucleus," Lancet, 337 (8738), (Feb. 16, 1991 ), pp. 403-406.

Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.

Christensen, Gary E., et al., "Volumetric transformation of brain anatomy," IEEE Transactions on Medical Imaging, 16 (6), (Dec. 1997), pp. 864-877.

Cooper, S , et al., "Differential effects of thalamic stimulation parameters on tremor and paresthesias in essential tremor," Movement Disorders, 17(Supp. 5), (2002), p. S193.

Coubes, P, et al., "Treatment of DYT1-generalised dystonia by stimulation of the internal globus pallidus," Lancet, 355 (9222), (Jun. 24, 2000), pp. 2220-2221.

Dasilva, A.F. M., et al., "A Primer Diffusion Tensor Imaging of Anatomical Substructures," Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

Finnis, K. W., et al., "3-D functional atalas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.

Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.

Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes in Computer Science; vol. 2489 (2002), pp. 69-76.

Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.

Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.

Gabriels, LA., et al., "Long-term electrical capsular stimulation in patients with obsessive-compulsive disorder," Neurosurgery, 52(6) (Jun. 2003), pp. 1263-1276.

Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

Goodall, E. V., et al., "Position-selective activation of peripheral nerve fibers with a cuff electrode," IEEE Transactions on Biomedical Engineering, 43(8) (Aug. 1996), pp. 851-856.

Goodall, E. V., "Simulation of activation and propagation delay during tripolar neural stimulation," Proceedings of the 15th Annual International Conference of the IEEE Engineering in Medicine and Biology Society (1993), pp. 1203-1204.

(56)         References Cited

OTHER PUBLICATIONS

Grill, WM., "Modeling the effects of electric fields on nerve fibers: influence of tissue electrical properties," IEEE Transactions on Biomedical Engineering, 46(8) (1999), pp. 918-928.

Grill, W. M., et al., "Neural and connective tissue response to long-term implantation of multiple contact nerve cuff electrodes," J Biomed Mater Res., 50(2) (May 2000), pp. 215-226.

Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.

Grill, W. M., et al., "Non-invasive measurement of the input-output properties of peripheral nerve stimulating electrodes," Journal of Neuroscience Methods, 65(1) (Mar. 1996), pp. 43-50.

Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.

Grill, W. M., "Spatially selective activation of peripheral nerve for neuroprosthetic applications," Ph.D. Case Western Reserve University, (1995), pp. 245 pages.

Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.

Grill, W. M., "Stimulus waveforms for selective neural stimulation," IEEE Engineering in Medicine and Biology Magazine, 14(4) (Jul.-Aug. 1995), pp. 375-385.

Grill, W. M., et al., "Temporal stability of nerve cuff electrode recruitment properties," IEEE 17th Annual Conference Engineering in Medicine and Biology Society, vol. 2 (1995), pp. 1089-1090.

Gross, RE., et al., "Advances in neurostimulation for movement disorders," Neurol Res., 22(3) (Apr. 2000), pp. 247-258.

Guridi et al., "The subthalamic nucleus, hemiballismus and Parkinson's disease: reappraisal of a neurological dogma," Brain, vol. 124, 2001, pp. 5-19.

Haberler, C, et al., "No tissue damage by chronic deep brain stimulation in Parkinson's disease," Ann Neurol., 48(3) (Sep. 2000), pp. 372-376.

Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.

Hanekom, "Modelling encapsulation tissue around cochlear implant electrodes," Med. Biol. Eng. Comput. vol. 43 (2005), pp. 47-55.

Haueisen, J , et al., "The influence of brain tissue anisotropy on human EEG and MEG," Neuroimage, 15(1) (Jan. 2002), pp. 159-166.

D'Haese et al. Medical Image Computing and Computer-Assisted Intervention—MICCAI 2005 Lecture Notes in Computer Science, 2005, vol. 3750, 2005, 427-434.

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.

Andrade-Souza, "Comparison of Three Methods of Targeting the Subthalamic Nucleus for Chronic Stimulation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008.

Mcintyre, Cameron , et al., "Finite element analysis of the current-density and electric field generated by metal microelectrodes", Ann Biomed Eng . 29(3), (2001 ),227-235.

Foster, K. R., et al., "Dielectric properties of tissues and biological materials: a critical review.", Grit Rev Biomed Ena. 17(1 ). {1989),25-104.

Limousin, P., et al., "Electrical stimulation of the subthalamic nucleus in advanced Parkinson's disease", N Engl J Med .. 339(16), (Oct. 15, 1998), 1105-11.

Kitagawa, M., et al., "Two-year follow-up of chronic stimulation of the posterior subthalamic white matter for tremor-dominant Parkinson's disease.", Neurosurgery. 56(2). (Feb. 2005),281-9.

Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.

Holsheimer, J. , et al., "Chronaxie calculated from current-duration and voltage-duration data", J Neurosci Methods. 97(1). (Apr. 1, 2000),45-50.

Hines, M. L., et al., "The Neuron simulation environment", Neural Comput. 9(6). (Aug. 15, 1997), 1179-209.

Herzog, J., et al., "Most effective stimulation site in subthalamic deep brain stimulation for Parkinson's disease", Mov Disord. 19(9). (Sep. 2004),1050-4.

Hershey, T., et al., "Cortical and subcortical blood flow effects of subthalamic nucleus stimulation in PD.", Neurology 61(6). (Sep. 23, 2003),816-21.

Hemm, S. , et al., "Evolution of Brain Impedance in Dystonic Patients Treated by GPi Electrical Stimulation", Neuromodulation 7(2) (Apr. 2004),67-75.

Hemm, S., et al., "Deep brain stimulation in movement disorders: stereotactic coregistration of two-dimensional electrical field modeling and magnetic resonance imaging.", J Neurosurg. 103(6): (Dec. 2005),949-55.

Haueisen, J, et al., "The influence of brain tissue anisotropy on human EEG and MEG", Neuroimage 15(1) (Jan. 2002),159-166.

Haslinger, B., et al., "Frequency-correlated decreases of motor cortex activity associated with subthalamic nucleus stimulation in Parkinson's disease.", Neuroimage 28(3). (Nov. 15, 2005),598-606.

Hashimoto, T. , et al., "Stimulation of the subthalamic nucleus changes the firing pattern of pallidal neurons", J Neurosci. 23(5). (Mar. 1, 2003),1916-23.

Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.

McNaughtan et al., "Electrochemical Issues in Impedance Tomography", 1st World Congress on Industrial Process Tomography, Buxton, Greater Manchester, Apr. 14-17, 1999.

Grill, WM., et al., "Electrical properties of implant encapsulation tissue", Ann Biomed Eng. vol. 22. (1994),23-33.

Grill, W. M., et al., "Deep brain stimulation creates an informational lesion of the stimulated nucleus", Neuroreport. 15I7t (May 19, 2004 ), 1137-40.

Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.

International Search Report and Written Opinion for PCT Application No. PCT/US2018/024568 mailed Jun. 4, 2018.

Official Communication for U.S. Appl. No. 15/937,264 mailed Sep. 16, 2020.

Official Communication for U.S. Appl. No. 15/937,264 mailed Mar. 22, 2021.

Official Communication for U.S. Appl. No. 15/937,264 mailed Sep. 3, 2021.

* cited by examiner

SYSTEMS AND METHODS FOR ESTIMATING A VOLUME OF ACTIVATION USING A COMPRESSED DATABASE OF THRESHOLD VALUES

CROSS-REFERENCE TO RELATED APPLICATIONS

This application is a continuation of U.S. Pat. No. 11,357, 986, filed Mar. 27, 2018, which claims benefit under 35 U.S.C. § 119(e) of U.S. Provisional Patent Application Ser. No. 62/480,942, filed Apr. 3, 2017, both of which are incorporated herein by reference

FIELD

The invention is directed to the field of electrical stimulation systems. The present invention is also directed to systems and methods for estimating a volume of activation, as well as methods of making and using systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. The electrodes can be formed into rings or segments disposed on a distal portion of the lead. The stimulus current projects from the electrodes. Using segmented electrodes can provide directionality to the stimulus current and permit a clinician to steer the current to a desired direction and stimulation field.

BRIEF SUMMARY

One embodiment is a system for estimating a volume of activation around an implanted electrical stimulation lead for a set of stimulation parameters. The system includes a display; and a processor coupled to the display and configured to: receive a set of stimulation parameters including a stimulation amplitude and a selection of one of more electrodes of the implanted electrical stimulation lead for delivery of the stimulation amplitude; determine an estimate of the volume of activation based on the set of stimulation parameters using the stimulation amplitude and a database including a plurality of planar distributions of stimulation threshold values and a map relating the planar distributions to spatial locations based on the one or more electrodes of the implanted electrical stimulation lead selected for delivery of the stimulation amplitude; and output, on the display, a graphical representation of the estimate of the volume of activation.

Another embodiment is a non-transitory computer-readable medium having computer executable instructions stored thereon that, when executed by at least one processor, cause the at least one processor to perform the instructions, the instructions including: receiving a set of stimulation parameters including a stimulation amplitude and a selection of one of more electrodes of the implanted electrical stimulation lead for delivery of the stimulation amplitude; determining an estimate of the volume of activation based on the set of stimulation parameters using the stimulation amplitude and a database including a plurality of planar distributions of stimulation threshold values and a map relating the planar distributions to spatial locations based on the one or more electrodes of the implanted electrical stimulation lead selected for delivery of the stimulation amplitude; and outputting, on the display, a graphical representation of the estimate of the volume of activation.

In at least some embodiments of the system or the non-transitory computer-readable medium, the database consists of the plurality of planar distributions, wherein each of the planar distributions is unique. In at least some embodiments, the database is a lossless compressed database. In at least some embodiments, the database is a lossy compressed database.

In at least some embodiments of the system or the non-transitory computer-readable medium, the map includes a plurality of entries, wherein each entry is indexed to a selection of the one or more electrodes and an angular location around the implanted electrical stimulation lead. In at least some embodiments, the selection of the one or more electrodes is characterized by at least one fractionalization parameter. In at least some embodiments, the at least one fractionalization parameter includes at least one of an axial position parameter, an angular direction parameter, or an angular spread parameter. In at least some embodiments, the selection of the one or more electrodes is characterized by an axial position parameter, an angular direction parameter, and an angular spread parameter. In at least some embodiments, at least two of the entries of the map point to a same planar distribution. In at least some embodiments of the system or the non-transitory computer-readable medium, the at least two of the entries include a first entry corresponding to a selection of a first one of the electrodes and a first angular location and a second entry corresponding to a selection of a second one of the electrodes and a second angular location, wherein the first angular location and the second angular location differ by a first angle, wherein a location of the first one of the electrodes differs from a location of the second one of the electrodes by the first angle.

Yet another embodiment is a system for estimating a volume of activation around an implanted electrical stimulation lead for a set of stimulation parameters. The system includes a processor configured to: receive a plurality of planar distributions of stimulation threshold values for each of a plurality of sets of stimulation parameters, each of the sets of stimulation parameters includes a stimulation amplitude and a selection of one of more electrodes of the implanted electrical stimulation lead for delivery of the stimulation amplitude; compress the plurality of planar distributions of stimulation threshold values into a compressed database including a plurality of unique planar distributions of stimulation threshold values; and generate a map relating the unique planar distributions of stimulation threshold values to the planar distributions of stimulation threshold values for the multiple sets of stimulation parameters.

In at least some embodiments, the compressing includes compress the plurality of planar distributions of stimulation threshold values into a compressed database using a lossless compression technique. In at least some embodiments, the compressing includes compress the plurality of planar distributions of stimulation threshold values into a compressed database using a lossy compression technique.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 9 is a schematic flowchart of a one embodiment of a method of estimating a volume of activation, according to the invention;

FIG. 10 is a schematic flowchart of one embodiment of a method of compressing a set of planar distributions of

Figure 11:
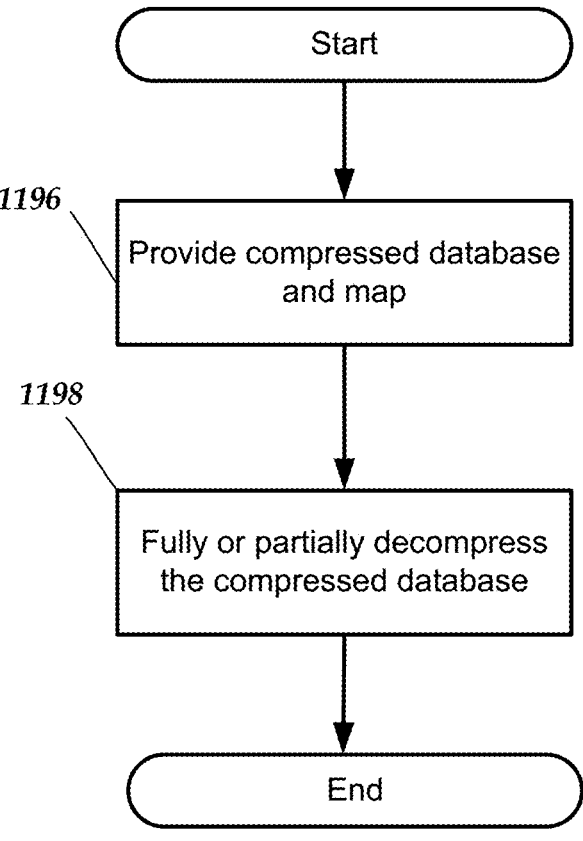

4 stimulation threshold values into a compressed database, according to the invention; and FIG. 11 is a schematic flowchart of one embodiment of a method of decompressing a compressed database, according to the invention.

DETAILED DESCRIPTION

The invention is directed to the field of electrical stimulation systems. The present invention is also directed to systems and methods for estimating a volume of activation, as well as methods of making and using systems.

A lead for electrical stimulation can include one or more stimulation electrodes. In at least some embodiments, one or more of the stimulation electrodes are provided in the form of segmented electrodes that extend only partially around the circumference of the lead. These segmented electrodes can be provided in sets of electrodes, with each set having electrodes radially distributed about the lead at a particular axial position. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglia stimulation, vagal nerve stimulation, basoreceptor stimulation, or stimulation of other nerves, organs, or tissues.

Suitable implantable electrical stimulation systems include, but are not limited to, at least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead can include both recording electrodes and stimulation electrodes or electrodes can be used for both recording and stimulation.

Figure 1:
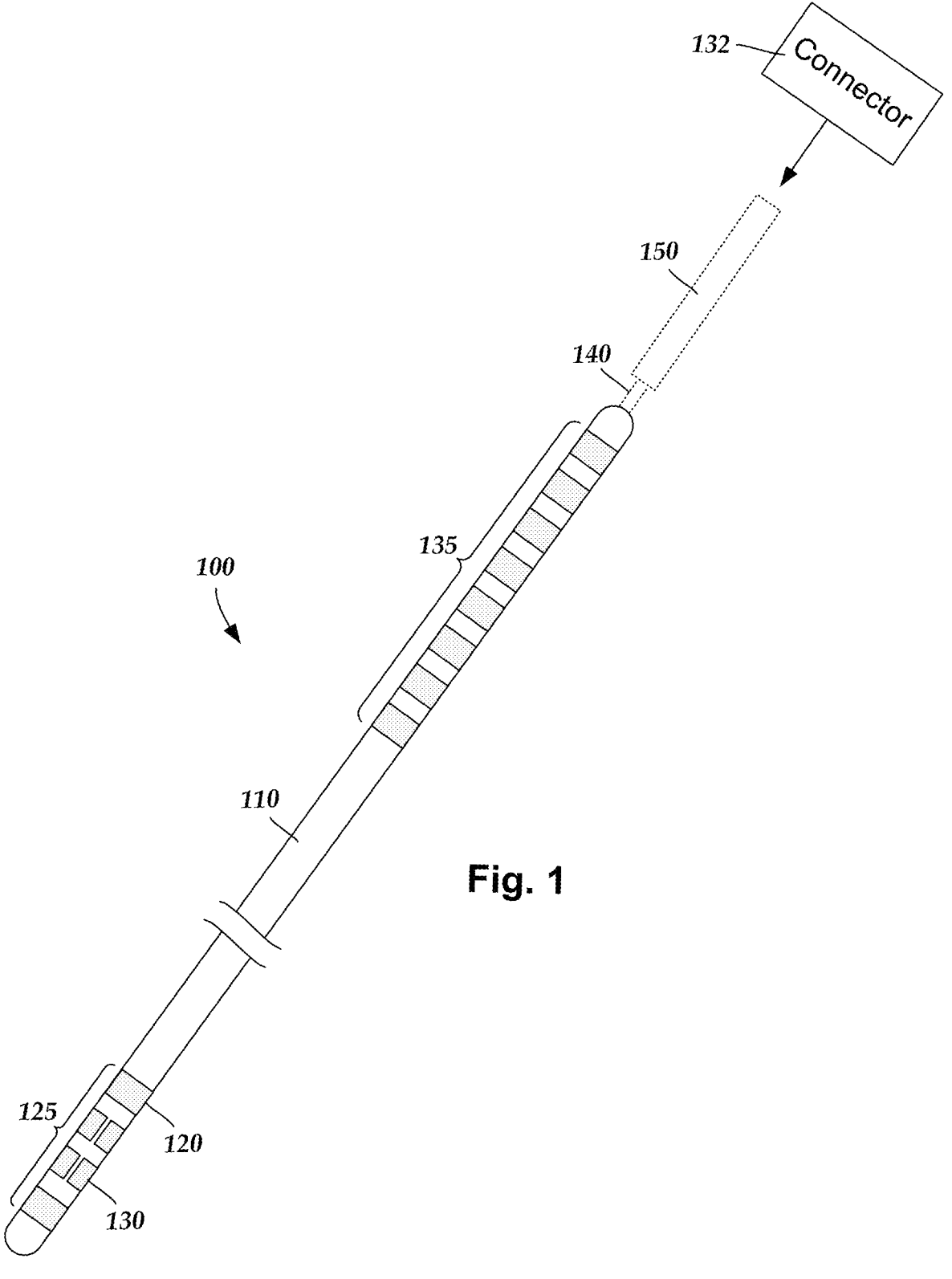
FIG. 1 is a schematic side view of one embodiment of a device for brain stimulation, according to the invention.

FIG. 1 illustrates one embodiment of a device 100 for electrical stimulation (for example, brain or spinal cord stimulation). The device includes a lead 110, a plurality of electrodes 125 disposed at least partially about a circumference of the lead 110, a plurality of terminals 135, a connector 132 for connection of the electrodes to a control module, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140. The connector 132 can be part of a control module or can be part of an optional lead extension that is coupled to the control module.

The control module (for example, control module 514 of FIG. 5) can be an implantable pulse generator that can be implanted into a patient's body, for example, below the patient's clavicle area. The control module can have eight stimulation channels which may be independently programmable to control the magnitude of the current stimulus from each channel. In some cases, the control module can have more or fewer than eight stimulation channels (e.g., 4-, 6-, 16-, 32-, or more stimulation channels). The control module can have one, two, three, four, or more connector ports, for receiving the plurality of terminals 135 at the proximal end of the lead 110. Examples of control modules are described in the references cited above.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control module or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulation energy to a selected angular range around the lead. When segmented electrodes are used in conjunction with an implantable control module that delivers constant current stimulus, current steering can be achieved to more precisely deliver the stimulus to one or more particular angular ranges around an axis of the lead.

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well. A lead that includes segmented electrodes can be referred to as a directional lead because the segmented electrodes can be used to direct stimulation along a particular direction or range of directions.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 can be disposed on any part of the lead body 110, usually near a distal end of the lead 100. In FIG. 1, the lead 100 includes two ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes can be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array, current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Applications Publication Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. Examples of leads with tip electrodes include at least some of the previously cited references, as well as U.S. Patent Applications Publication Nos. 2014/0296953 and 2014/0343647, all of which are incorporated herein by reference in their entireties.

The lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires couple the electrodes 120, 130 to the terminals 135.

Figures 3A, 3B, 3C, 3D:
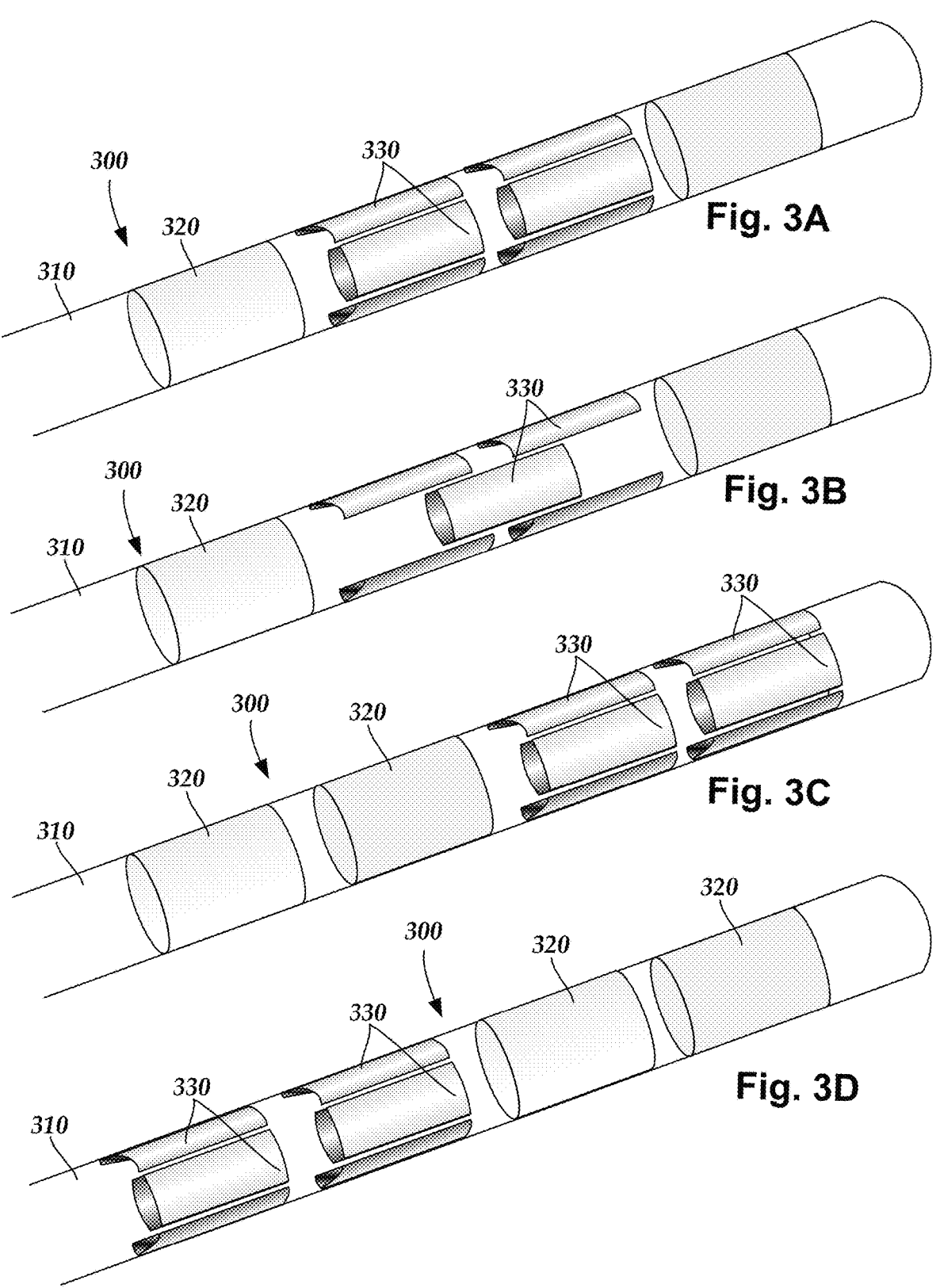
FIG. 3A is a perspective view of an embodiment of a portion of a lead having a plurality of segmented electrodes, according to the invention.
FIG. 3B is a perspective view of a second embodiment of a portion of a lead having a plurality of segmented electrodes, according to the invention.
FIG. 3C is a perspective view of a third embodiment of a portion of a lead having a plurality of segmented electrodes, according to the invention.
FIG. 3D is a perspective view of a fourth embodiment of a portion of a lead having a plurality of segmented electrodes, according to the invention.

When the lead 100 includes both ring electrodes 120 and segmented electrodes 130, the ring electrodes 120 and the segmented electrodes 130 may be arranged in any suitable configuration. For example, when the lead 100 includes two ring electrodes 120 and two sets of segmented electrodes 130, the ring electrodes 120 can flank the two sets of segmented electrodes 130 (see e.g., FIGS. 1, 3A, and 3E-3H—ring electrodes 320 and segmented electrode 330). Alternately, the two sets of ring electrodes 120 can be disposed proximal to the two sets of segmented electrodes 130 (see e.g., FIG. 3C—ring electrodes 320 and segmented electrode 330), or the two sets of ring electrodes 120 can be disposed distal to the two sets of segmented electrodes 130 (see e.g., FIG. 3D—ring electrodes 320 and segmented electrode 330). One of the ring electrodes can be a tip electrode (see, tip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Figures 3E, 3F, 3G:
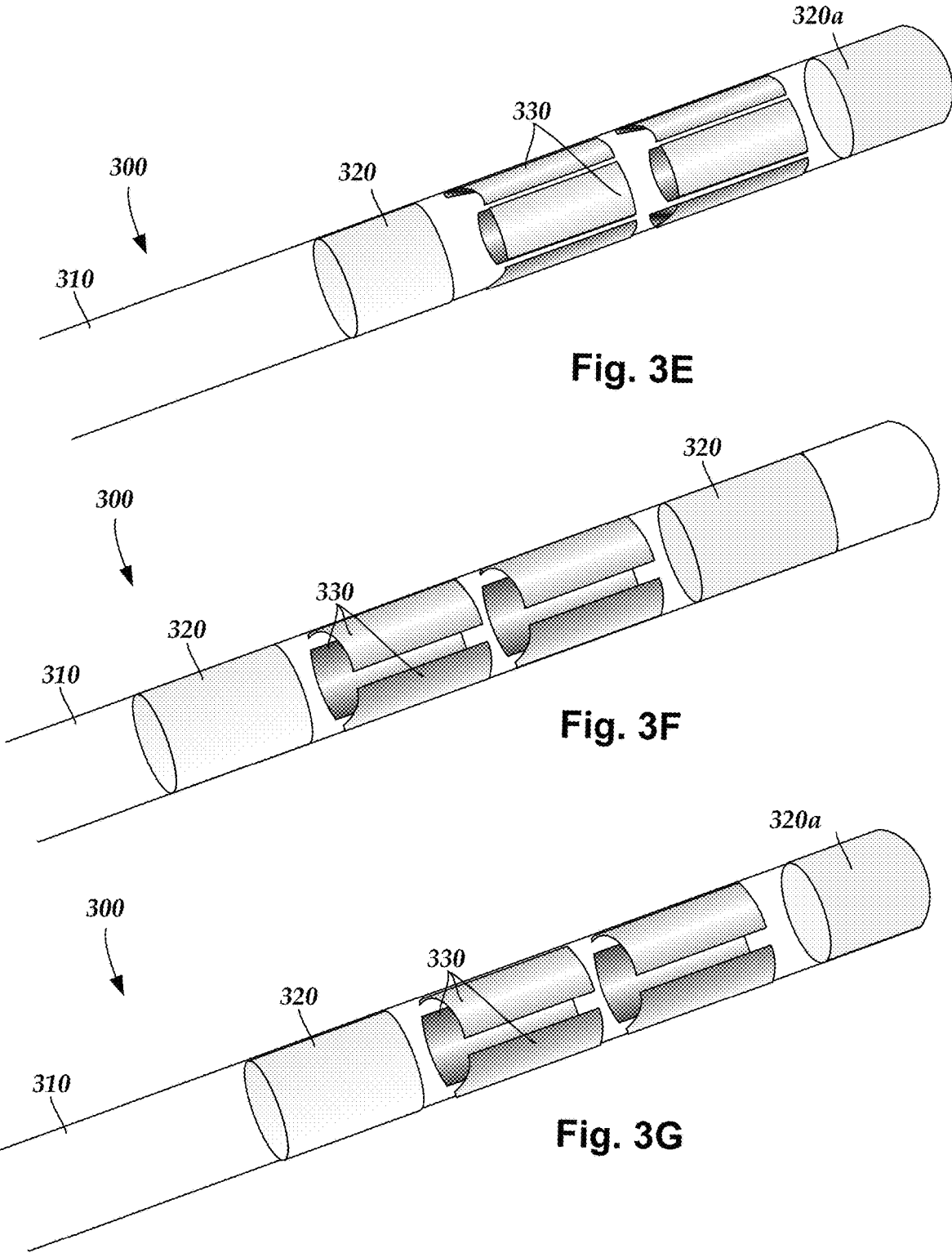
FIG. 3E is a perspective view of a fifth embodiment of a portion of a lead having a plurality of segmented electrodes, according to the invention.
FIG. 3F is a perspective view of a sixth embodiment of a portion of a lead having a plurality of segmented electrodes, according to the invention.
FIG. 3G is a perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E—ring electrodes 320 and segmented electrode 330). It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F, 3G, and 3H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F, 3G, and 3H has two sets of segmented electrodes, each set containing three electrodes disposed around the circumference of the lead, flanked by two ring electrodes (FIGS. 3F and 3H) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
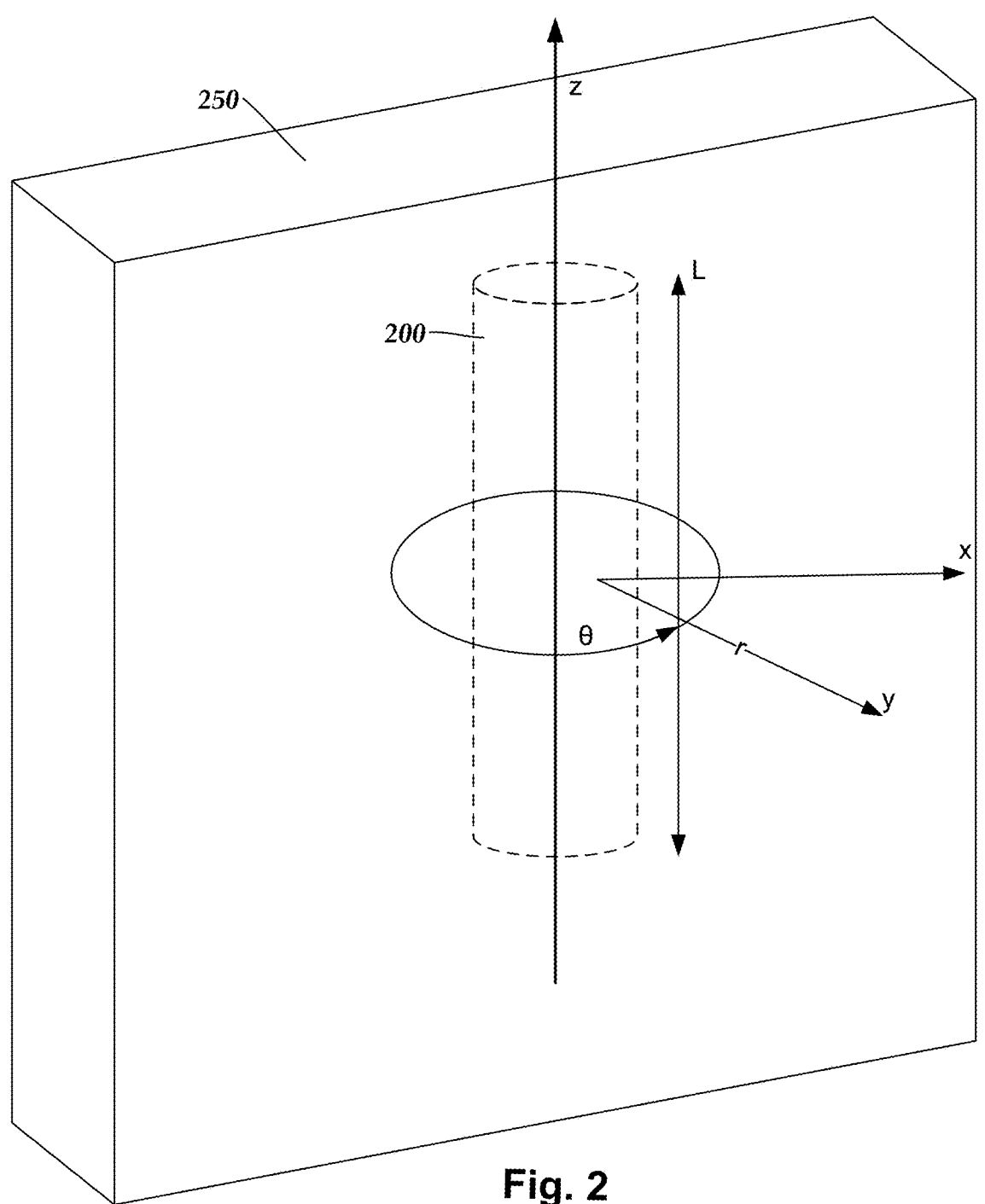
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the stimulation can be shifted at each level along the length L of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes in a set are utilized to allow for true 360° selectivity.

Turning to FIGS. 3A-3H, when the lead 300 includes a plurality of sets of segmented electrodes 330, it may be desirable to form the lead 300 such that corresponding electrodes of different sets of segmented electrodes 330 are radially aligned with one another along the length of the lead 300 (see e.g., the segmented electrodes 330 shown in FIGS. 3A and 3C-3G). Radial alignment between corresponding electrodes of different sets of segmented electrodes 330 along the length of the lead 300 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 300 are radially aligned with one another and do not radially shift in relation to one another during manufacturing of the lead 300.

In other embodiments, individual electrodes in the two sets of segmented electrodes 330 are staggered (see, FIG. 3H) relative to one another along the length of the lead body 310. In some cases, the staggered positioning of corresponding electrodes of different sets of segmented electrodes along the length of the lead 300 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

Figure 3H:
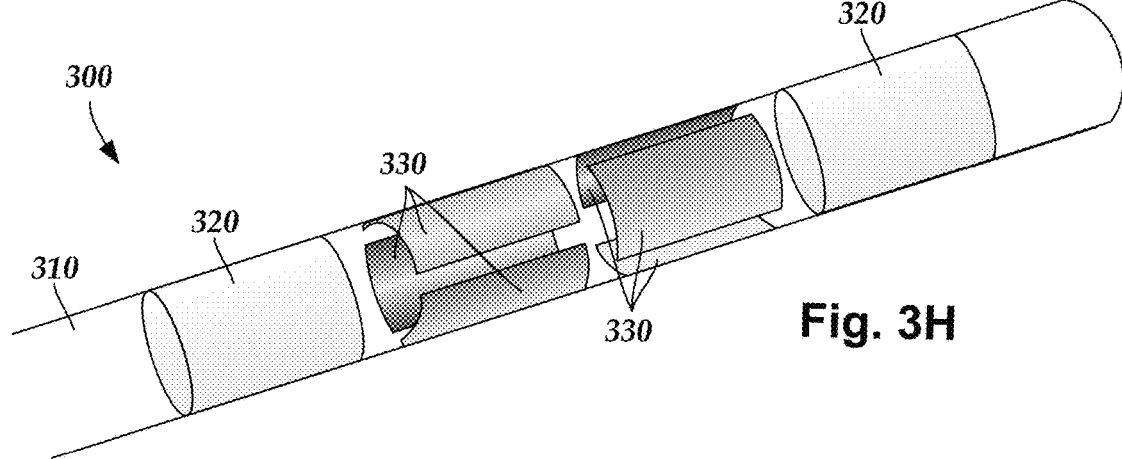
FIG. 3H is a perspective view of an eighth embodiment of a portion of a lead having a plurality of segmented electrodes, according to the invention.

FIGS. 3A-3H illustrate leads 300 with segmented electrodes 330, optional ring electrodes 320 or tip electrodes 320a, and a lead body 310. The sets of segmented electrodes 330 each include either two (FIG. 3B), three (FIGS. 3E-3H), or four (FIGS. 3A, 3C, and 3D) or any other number of segmented electrodes including, for example, three, five, six, or more. The sets of segmented electrodes 330 can be aligned with each other (FIGS. 3A-3G) or staggered (FIG. 3H)

Any other suitable arrangements of segmented electrodes can be used. As an example, arrangements in which segmented electrodes are arranged helically with respect to each other. One embodiment includes a double helix.

Figure 5:
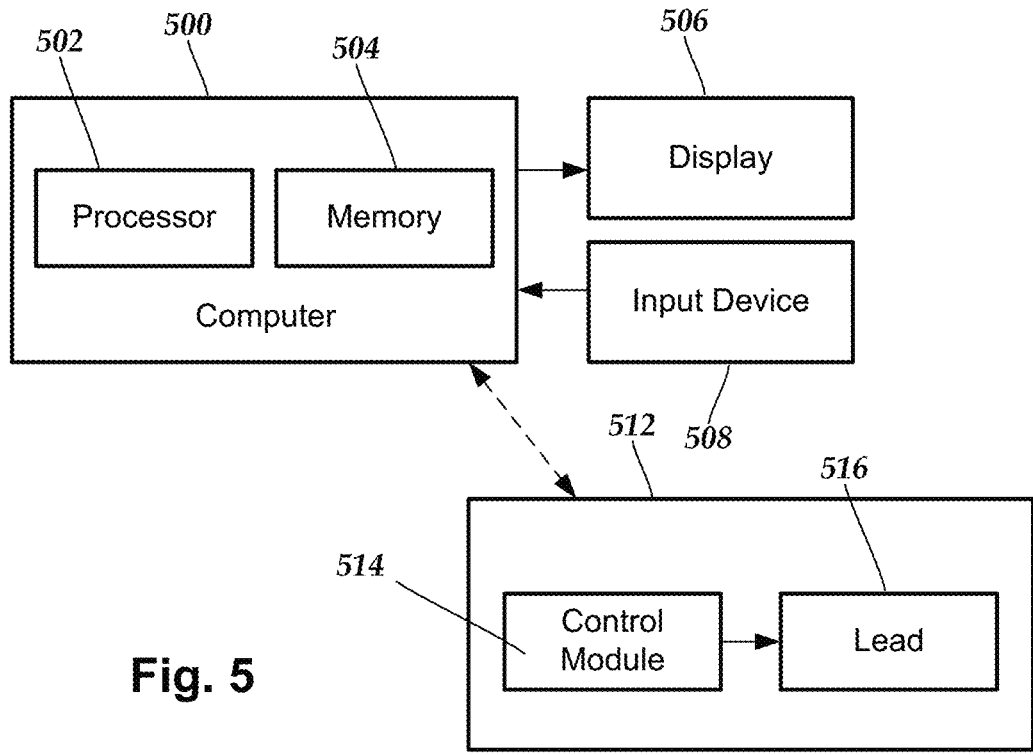
FIG. 5 is a schematic illustration of one embodiment of a system for practicing the invention.

FIG. 5 illustrates one embodiment of a system for practicing the invention. The system can include a computer 500 or any other similar device that includes a processor 502 and a memory 504, a display 506, an input device 508, and, optionally, the electrical stimulation system 512.

The computer 500 can be a laptop computer, desktop computer, tablet, mobile device, smartphone or other devices that can run applications or programs, or any other suitable device for processing information and for presenting a user interface. The computer can be, for example, a clinician programmer, patient programmer, or remote programmer for the electrical stimulation system 512. The computer 500 can be local to the user or can include components that are non-local to the user including one or both of the processor 502 or memory 504 (or portions thereof). For example, in some embodiments, the user may operate a terminal that is connected to a non-local computer. In other embodiments, the memory can be non-local to the user.

The computer 500 can utilize any suitable processor 502 including one or more hardware processors that may be local to the user or non-local to the user or other components of the computer. The processor 502 is configured to execute instructions provided to the processor, as described below.

Any suitable memory 504 can be used for the computer 502. The memory 504 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 506 can be any suitable display device, such as a monitor, screen, display, or the like, and can include a printer. The input device 508 can be, for example, a keyboard, mouse, touch screen, track ball, joystick, voice recognition system, or any combination thereof, or the like and can be used by the user to interact with a user interface or clinical effects map.

The electrical stimulation system 512 can include, for example, a control module 514 (for example, an implantable pulse generator) and a lead 516 (for example, the lead illustrated in FIG. 1.) The electrical stimulation system 512 may communicate with the computer 500 through a wired or wireless connection or, alternatively or additionally, a user can provide information between the electrical stimulation system 512 and the computer 500 using a computer-readable medium or by some other mechanism. In some embodiments, the computer 500 may include part of the electrical stimulation system.

In at least some instances, a treating physician may wish to tailor the stimulation parameters (such as which one or more of the stimulating electrode contacts to use, the stimulation pulse amplitude (such as current or voltage amplitude depending on the stimulator being used,) the stimulation pulse width, the stimulation frequency, or the like or any combination thereof) for a particular patient to improve the effectiveness of the therapy. Electrical stimulation systems can provide an interface that facilitates parameter selections. Examples of such systems and interfaces can be found in, for example, U.S. Pat. Nos. 8,326,433; 8,831,731; 8,849,632; 9,050,470; and 9,072,905; and U.S. Patent Application Publication No. 2014/0277284, all of which are incorporated herein by reference in their entireties.

Stimulation region visualization systems and methods can be used to predict or estimate a region of stimulation for a given set of stimulation parameters. In at least some embodiments, the systems and methods further permit a user to modify stimulation parameters and visually observe how such modifications can change the predicted or estimated stimulation region. Such algorithms and systems may provide greater ease of use and flexibility and may enable or enhance specific targeting of stimulation therapy. The term "volume of activation" (VOA) will be used to designate an estimated region of tissue that will be stimulated for a particular set of stimulation parameters. The terms "stimulation field map" (SFM) and "volume of tissue activation" (VTA) also refer to the VOA. Examples of methods for determining the VOA can be found in, for example, U.S. Pat. Nos. 7,346,282; 8,180,601; 8,209,027; 8,326,433; 8,589, 316; 8,594,800; 8,606,360; 8,675,945; 8,831,731; 8,849, 632; 8,958,615; 9,020,789; and U.S. Patent Application Publications Nos. 2009/0287272; 2009/0287273; 2012/ 0314924; 2013/0116744; 2014/0122379; 2015/0066111; and 2016/0030749, all of which are incorporated herein by reference.

In at least some methods of estimating or determining a VOA, the electric field arising from the electrical energy delivered according to the stimulation parameters is determined or modeled, the tissue response to an electrical field is also determined or modeled, and then the VOA can be identified or estimated. There are a variety of methods for determining or modeling an electric field including, but not limited to, a finite element analysis model described in, for example, the references cited in the preceding paragraph, although it will be recognized that other models (including other models described in the references cited in the preceding paragraph) can also be used. There are also a variety of method for determining or modeling tissue including, but not limited to, a neural element model or axon model as described in, for example, the references cited in the preceding paragraph, although it will be recognized that other models (including other models described in the references cited in the preceding paragraph) can also be used.

Figure 4A:
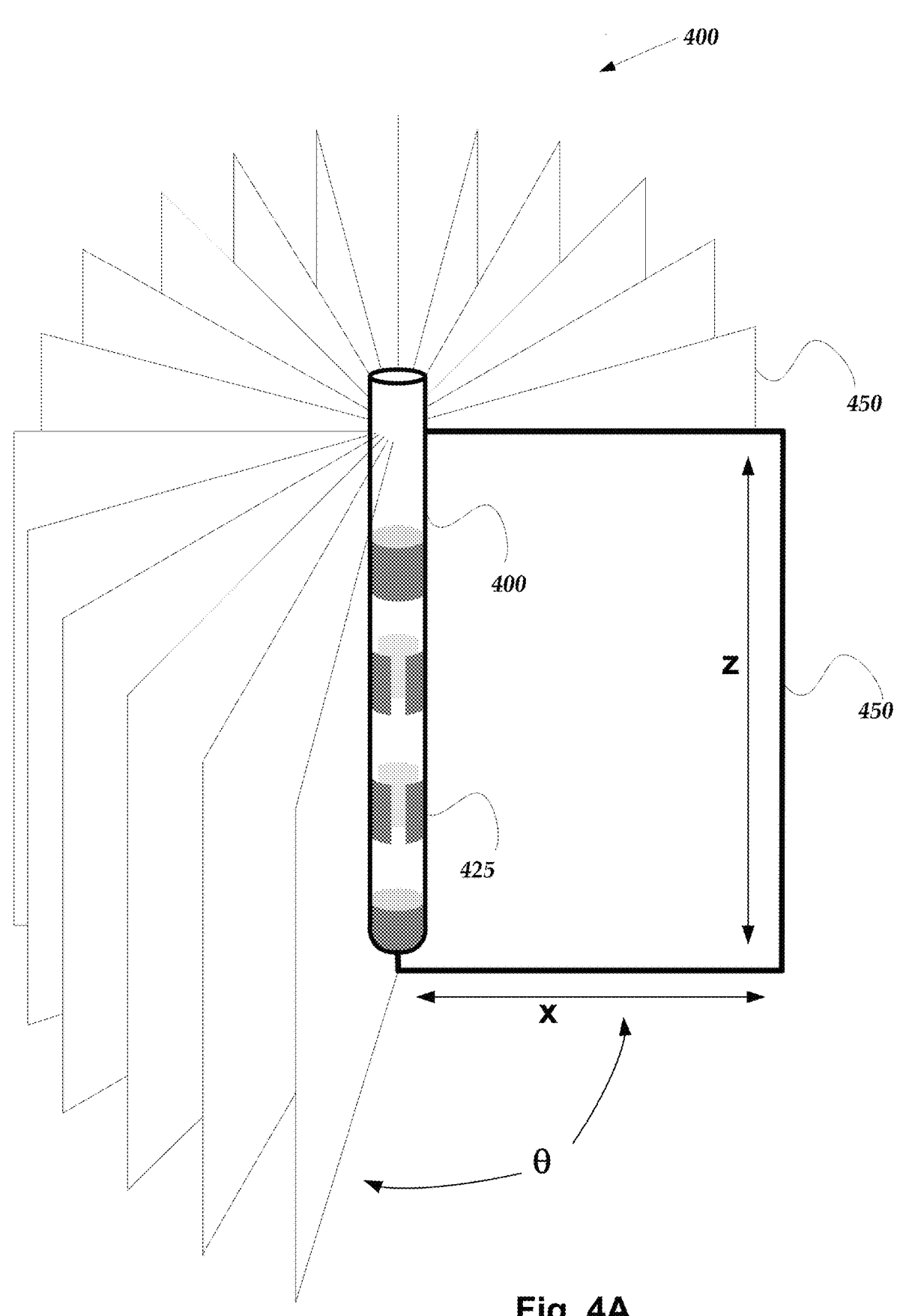
FIG. 4A is a graphical illustration of one embodiment of a set of planes relative to a lead for facilitating estimating a volume of activation, according to the invention.

In at least some embodiments, the information based on the electric field model and tissue response model can be used to produce planar distributions of stimulation threshold values for a series of planes 450 distributed around a lead 400 having electrodes 425, as illustrated in FIG. 4A. In at least some embodiments, these stimulation threshold values may be dependent on other stimulation parameters, such as stimulation duration (for example, pulse width), stimulation frequency, and the like.

Figure 4B:
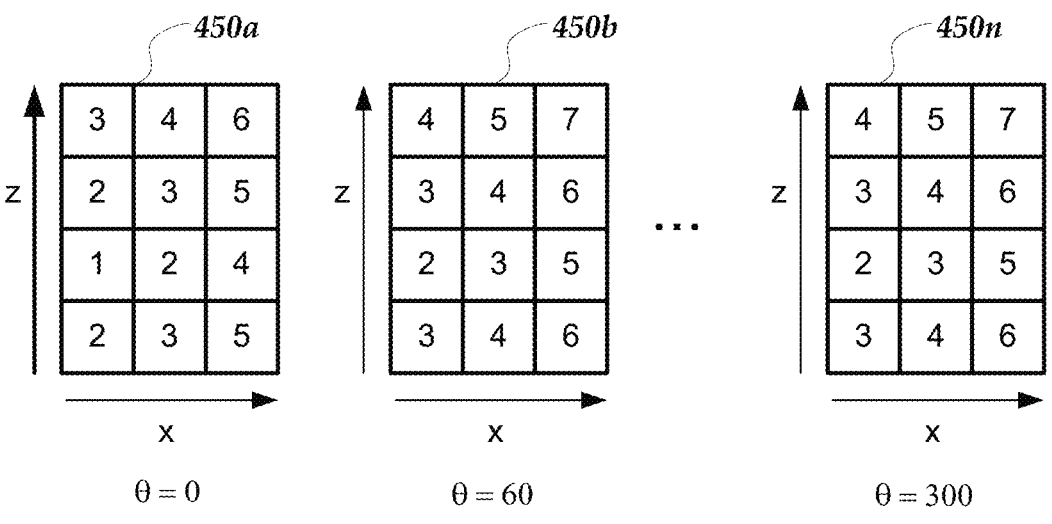
FIG. 4B illustrates examples of planar distributions of stimulation threshold values, according to the invention.

Each of the planes 450 can be divided into multiple regions (for example, squares or rectangles) with an associated stimulation threshold value (such as a threshold current or voltage) which, when applied to the lead will activate or stimulate the tissue at that region, as illustrated in FIG. 4B. For discussion purposes, the stimulation threshold value will be considered a threshold current, $I_{th}$, but it will be recognized that a threshold voltage or other electrical characteristic may be used instead. Each region of each plane 450 can be characterized by an x-value, which corresponds to a radial distance from the lead 400, a z-value, which corresponds to an axial coordinate along the longitudinal axis of the lead, and a θ-value, which corresponds to the relative angle of the plane in which the region resides. These coordinates are labeled in FIGS. 4A and 4B. Thus, the values of $I_{th}$ can be stored in a database as a series of $I_{th}$ tables, $I_{th}(z, x, \theta)$, which can also be indexed relative to other state variables, as described below. A visual example of these $I_{th}$ tables 450a, 450b, 450n is presented in FIG. 4B where each plane 450 of FIG. 4A represents one of the tables 450a, 450b, . . . 450n wherein the number in each cell of the table represents the current at which a neural fiber located at the center of the cell would be activated. Although the example illustrated in FIG. 4B has four z values, 3 x values, and one table for every 60 degrees of θ, it will be recognized that the number of values for z and x and the θ separation for each table can be any number. The tables of FIG. 4B are merely provided for illustrative purposes.

The $I_{th}$ values may also depend on other stimulation parameters, such as pulse width ("pw"), pulse frequency ("freq"), and the distribution of the electrical energy (or current or voltage) between the different electrodes (which can be referred to as "fractionalization"). Thus, when these factors are considered, the database is expanded to $I_{th}(z, x, \theta, pw, freq, fractionalization)$. Other stimulation parameters may be added to this set. The database may also be visualized as a set of tables 450a, 450b, . . . 450n (as illustrated in FIG. 4B) for each unique selection of the pulse width, frequency, and fractionalization parameters.

Fractionalization is the distribution of the electrical energy (or current or voltage) between the electrodes of the lead and can be expressed, for example, by an additional set of parameters: axial position, rotation, and spread. For purposes of illustration of these three parameters, one embodiment of a distal end of a lead 500 is presented in FIG. 6. The lead 500 includes a ring electrode 550, a first set of three segmented electrodes 552a, 552b, 552c, a second set of three segmented electrodes 554a, 554b, 554c, and a tip electrode 556. An "axial position" variable can be used to estimate or represent the central axial position of the field relative to the longitudinal axis of the lead. For example, if the stimulation is provided solely by ring electrode 550, then the axial position of the field is centered on the axial position of the ring electrode 550. However, combinations of electrodes can also be used. For example, if the stimulation is provided with 50% of the current amplitude on ring electrode 550 and 50% of the current amplitude on segmented electrode 552a, then the axial position of the field can be described as centered axially between electrode 550 and electrode 552a (although it will be recognized that the field also extends in both axial directions from this axial position.) If the stimulation is provided with 75% of the current amplitude on ring electrode 550 and 25% of the current amplitude on segmented electrode 552a, then the axial position of the field can be described as centered axially between electrode 550 and electrode 552a, but closer to ring electrode 550. In at least some embodiments, a specific number of different axial position values can be defined for the system.

Figure 6:
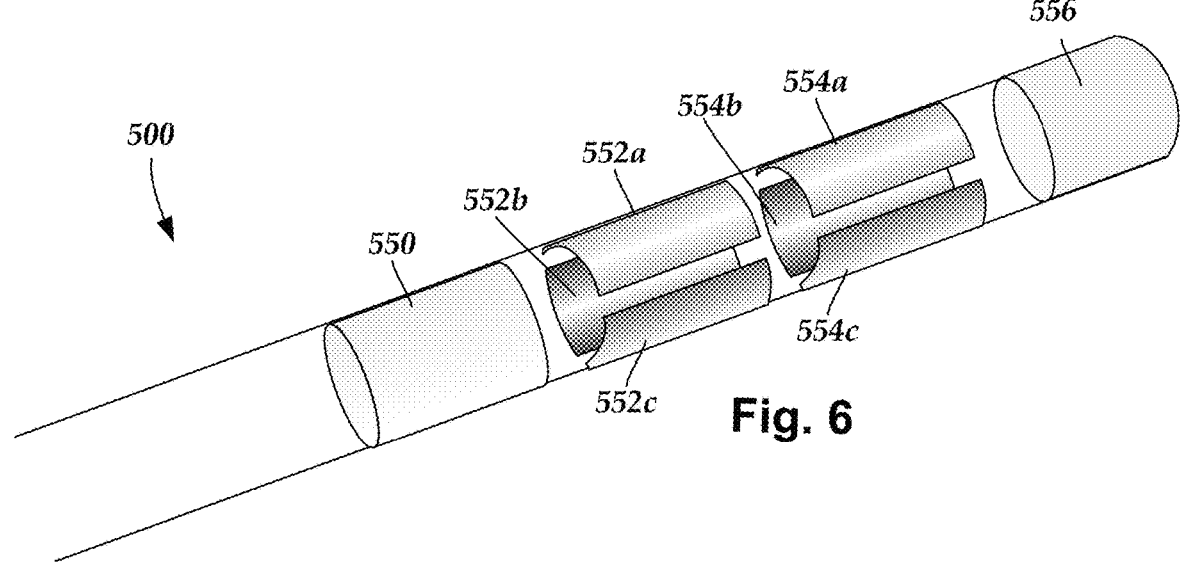
FIG. 6 is a perspective view of a portion of a lead having a plurality of segmented electrodes for use as an example, according to the invention.

For example, in one embodiment, 31 different axial position values can be defined for the lead illustrated in FIG. 6. Four of the axial positions correspond to 1) electrode 550, 2) electrodes 552a, 552b, 552c, 3) electrodes 554a, 554b, 554c, and 4) electrode 556. In addition, nine axial positions can be defined between adjacent pairs of these four axial positions (e.g., 1) 90% of current amplitude on electrode 550 and 10% of current amplitude on electrodes 552a, 552b, 552c, 2) 80% on electrode 550 and 20% on electrodes 552a, 552b, 552c, . . . 8) 20% on electrode 550 and 80% on electrodes 552a, 552b, 552c, and 9) 10% on electrode 550 and 90% on electrodes 552a, 552b, 552c).

Another parameter is "rotation" which represents the angular direction of the field extending away from the lead. In the case of stimulation provided solely by ring electrode 550, the rotation parameter is arbitrary because the stimulation is provided equally in all directions. On the other hand, if the stimulation is provided by segmented electrode 552a, the rotation can be described as directed outward from segmented electrode 552a. Again, combinations of electrodes can be used so that the rotation may be described as centered between electrodes 552a, 552b if 50% of the stimulation amplitude is provided to both electrodes. In at least some embodiments, a specific number of different rotation values can be defined for the system.

For example, in one embodiment, 12 different rotation values are defined for the lead illustrated in FIG. 6. For example, three of the rotation values correspond to the angular positions of 1) electrodes 552a, 554a, 2) electrodes 552b, 554b, and 3) electrodes 552c, 554c. In addition, three additional rotation values can be defined between adjacent pairs of these three rotation values (e.g., 1) 75% on electrode 552a and 25% on electrode 552b, 2) 50% on electrode 552a and 50% on electrode 552b; and 3) 25% on electrode 552a and 75% on electrode 552b).

Yet another parameter is "spread" which relates to the angular spread of the field around the circumference of the lead. In the case of stimulation provided solely by ring electrode 550, the spread variable is at a maximum because the stimulation is provided equally in all directions. On the other hand, if the stimulation is provided by segmented electrode 552a, the spread variable is at its minimum because the field is generated using only one segmented electrode 552a. Again, combinations of electrodes can be used. For example, the spread may be described as intermediate between the two previous examples when 50% of the stimulation amplitude is provided on both electrodes 552a, 552b. In at least some embodiments, a specific number of different spread values can be defined for the system.

For example, in one embodiment, 11 different spread values are defined for the lead illustrated in FIG. 6. For example, one spread value corresponds an equal field in all directions (such as, the field generated by electrode 550 or electrode 556) and another spread value corresponds to a field generated by one of the segmented electrodes (e.g., electrode 552a). The other nine spread values are between these two extremes.

The stimulation (e.g., stimulation current) can be steered to different positions and arrangements around the lead which results in changes in these fractionalization parameters: axial position, rotation, and spread. For example, the stimulation can be moved up or down the longitudinal axis of the lead thereby changing the axial position parameter. As an example, the stimulation can be initially provided 100% through electrode 550. The stimulation can then be steered distally by directing a portion of the stimulation to the electrodes 552a, 552b, 552c. For example, in a first step, 90% of the stimulation remains on electrode 550 and 10% is divided equally among electrodes 552a, 552b, 552c. The second step can have 80% on electrodes 550 and 20% divided equally among electrodes 552a, 552b, 552c. This can continue until there is no stimulation on electrode 550 and 100% of the stimulation is divided among electrodes 552a, 552b, 552c. The process can proceed to incrementally transfer stimulation from electrodes 552a, 552b, 552c to electrodes 554a, 554b, 554c. Similarly, the stimulation then be incrementally transferred from electrodes 554a, 554b, 554c to electrode 556.

The stimulation can also be rotated. For example, stimulation from electrode 552a can be rotated to electrode 552b in stepped increments. The stimulation field can also be spread. For example, stimulation field from electrode 552a can be spread so that the stimulation arises from both electrodes 552a, 552b. That stimulation field can then be contracted so that the stimulation is only from electrode 552b.

It will be recognized that the resulting $I_{th}$ database can be quite large depending on the number of different values for each of the parameters. As one example, such an $I_{th}$ database can be generated for a set of fractionalization states obtained using 11 different spread values, 12 different rotation values, and 31 different axial position values, as well as multiple values of the other variables (for example, 43 values for z, 16 values for r, 12 values for θ, 12 values for pulse width, and 45 values for frequency).

The database can be compressed using one or more techniques. As one example, the database can be compressed (for example, the amount of stored data decreased) when it is recognized that many fractionalization states are not unique or are not available. The amount of data stored can be reduced by taking advantage of the unavailability of fractionalization states, as well as redundancy and symmetry in the fractionalization states. In at least some embodiments, the database can be reduced to a set of unique $I_{th}$ tables (such as those illustrated in FIG. 4B) and a map M which relates the $I_{th}$ tables to the different fractionalizations (i.e., the different axial position, rotation, and spread values) and, optionally, to different pulse widths or frequencies.

Using lead 500 of FIG. 6 as an example with 11 different spread values, 12 different rotation values, and 31 different axial position values, as described above, there are potentially 4092 different fractionalization states. However, a number of these states are not actually available or are redundant. For example, any stimulation that utilizes only ring electrode 550 for delivery of the stimulation will have the maximum spread value (because the other spread states, with a smaller degree of spread, cannot be produced using only the ring electrode 550) and rotation value will be irrelevant because there is no identifiable angular direction of the stimulation because stimulation by the ring electrode 550 is cylindrically symmetric. Although there are potentially 121 different possible combinations of spread and rotation for each axial position value, when the axial position value corresponds to stimulation using the ring electrode only, there is only 1 non-redundant fractionalization state. Thus, the number of actual available fractionalization states associated with stimulation using only one of the ring electrodes is reduced by 120.

As another example, when the stimulation is divided equally among 552a, 552b, 552c (i.e., the spread variable value is maximum), then the rotation value is again irrelevant because there is no identifiable angular direction for the stimulation and therefore, although there are 12 potential selections of rotation, there is actually only 1 available rotation state. Thus, the number of actual available states associated with stimulation using maximum spread over all of the segmented electrodes of one set is reduced by 12.

Using similar observations, it is found that, for 31 axial position values, 12 rotation values, and 11 spread values and assuming symmetrical tissue response, the 4092 total states can be reduced to 828 unique fractionalization states that can be selected for the electrodes of the lead in FIG. 6.

In addition to reducing the number of unique or possible fractionalization states, symmetry can be used to compress the stored data. Assuming that the tissue response is the same in all directions, then the $I_{th}$ values for stimulation using only electrode 552a (fractionalization state 1) will be the same as the $I_{th}$ values for stimulation using only electrode 552b (fractionalization state 2) except for a 120 degree rotation and will be the same as the $I_{th}$ values for stimulation using electrode 552c (fractionalization state 3) except for a $-120$ degree rotation. In other words, $I_{th,1}(x, z, \theta)=I_{th,2}(x, z, \theta-120)=I_{th,3}(x, z, \theta+120)$ where $I_{th,1}=$the threshold table for fractionalization state 1, $I_{th,2}=$the threshold table for fractionalization state 2, and $I_{th,3}=$the threshold table for fractionalization state 3. Because of this symmetry, only one set of $I_{th}$ tables is stored for these three fractionalization states because the same set of $I_{th}$ tables by mapping the $I_{th}$ tables accounting for the rotation described above. Thus, the number of $I_{th}$ tables needed in the database is less due to the recognition of the symmetry. This equivalence of the $I_{th}$ tables, except for a rotation, for similar states is available for many fractionalizations. For example, a fractionalization that includes stimulation provided by a combination of electrode 556 and electrode 554a (with a particular apportioning of the stimulation between the two electrodes, for example, 70%/30%) is similar to stimulation provided by a combination of electrode 556 and electrode 554b (with the same apportioning of the stimulation between the two electrodes) except for a rotation of 120 degrees. In this example, the same set of $I_{th}$ tables can be used with the mapping taking into account the rotation. As another example, stimulation provided by a combination of electrodes 554a and 554b (with a particular apportioning of the stimulation between the two electrodes, for example, 70%/30%) is similar to a combination of electrodes 554b and 554c (with the same apportioning of the stimulation between the two electrodes) except for a rotation of 120 degrees. Again, in this example, the same set of $I_{th}$ tables can be used with the mapping taking into account the rotation.

Similarly, in many instances the stimulation field will have mirror symmetry about the central radial axis of the stimulation field. In other words, $I_{th}(x, z, \theta)=I_{th}(x, z, -\theta)$ and, therefore, in these instances, only $I_{th}(x, z, \theta)$ for values of $\theta$ from 0 to 180 degrees needs to be stored in the database because $I_{th}(x, z, \theta)$ for values of $\theta$ between 180 and 360 degrees, non-inclusive of the endpoints, corresponds to one of the stored $I_{th}(x, z, \theta)$. Again, a map can be used to map the stored $I_{th}$ tables to the large set of $I_{th}(x, z, \theta$, fractionalization), but the number of $I_{th}$ tables that are need to be stored in the database is less due to the recognition of the symmetry.

Figure 7:
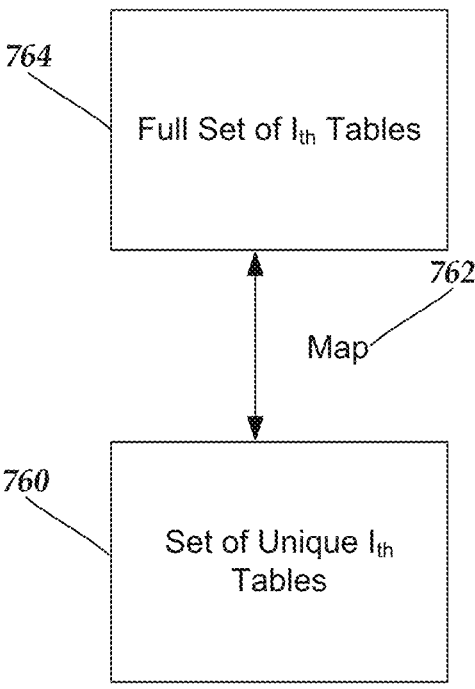
FIG. 7 is a schematic representation of relationship between a full set of $I_{th}$ tables and a compressed set of unique $I_{th}$ tables related by a map, according to the invention.

It will be recognized that other symmetries can be identified and that there may also be symmetries that are applicable based on pulse width or frequency stimulation parameters. Therefore, as illustrated in FIG. 7, a set of unique $I_{th,unique}$ tables 760 (such as $I_{th,unique}(X, z, \theta)$) form a compressed database and are identified, as well as a map 762 that relates the $I_{th,unique}$ tables to the full set of $I_{th}$, full tables 764 (such as $I_{th,full}(x, z, \theta$, fractionalization) or $I_{th,full}(x, z, \theta$, fractionalization, pw, frequency)). This arrangement is a lossless compression of the $I_{th}$ data because the full set of $I_{th}$ data can be reconstructed from the $I_{th,unique}$ tables and map.

Figure 8:
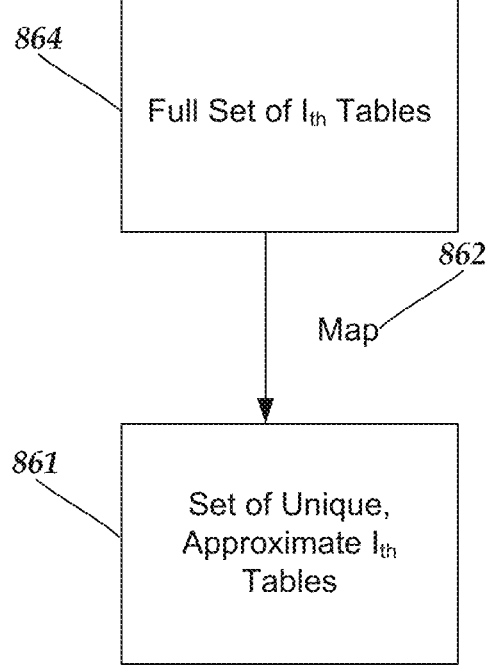
FIG. 8 is a schematic representation of relationship between a full set of $I_{th}$ tables and a compressed set of unique, approximate $I_{th}$ tables related by a map, according to the invention.

Alternatively or additionally, lossy compression may also be applied to the $I_{th,unique}$ tables or full $I_{th}$ data. As illustrated in FIG. 8, a set of unique, approximate $I_{th,approx}$ tables 861 form a compressed database and are identified with a map 862 that relates the $I_{th,approx.}$ tables to the $I_{th,full}$ tables 860. This is a lossy compression because the $I_{th,approx.}$ tables 861 are not necessarily the same as the $I_{th,full}$ tables that they represent, but rather the $I_{th,approx.}$ tables are sufficiently similar (based on a similarity metric) to the original $I_{th,full}$ tables that they represent to be acceptable to the user.

In some embodiments of lossy compression, a group of similar $I_{th}$ tables are approximated using a single $I_{th,approx}$ table. As an example, a similarity metric may be used to compare a particular $I_{th}$ table with a particular $I_{th,approx.}$ table and, when the similarity metric is within a specified tolerance, the original $I_{th}$ table can be represented by the $I_{th, approx.}$ table in the compressed $I_{th}$ database. In this manner, the large set of $I_{th}$ tables can be represented by fewer $I_{th,approx}$ tables. Any suitable similarity metric can be used including, but not limited to, the sum of the of the squared differences between corresponding entries in the $I_{th}$ table and the $I_{th,approx.}$ table. Moreover, any suitable number of $I_{th,approx.}$ tables can be selected including 10, 50, 100, 200, 300, 400, 500 or more tables.

Another lossy compression method utilizes MPEG compression or a process similar to MPEG compression. MPEG video compression is a procedure that looks at the differences from frame to frame in a video sequence and, instead of generating data describing each frame, generates data describing differences from the previous frame.

In one example of a lossy compression method for $I_{th}$ data, a similarity metric is selected such as the sum of the of the squared differences between corresponding entries in a particular $I_{th}$ table and a selected base $I_{th}$ table. A sequence of $I_{th}$ tables can then be built from this base $I_{th}$ table. In some embodiments, an ordered list is created starting with the $I_{th}$ tables most similar to the base $I_{th}$ table and continuing to less similar $I_{th}$ tables. This can generate a linear succession of $I_{th}$ tables. In other embodiments, a branched sequence of $I_{th}$ tables can be created by building a connected non-looping sequence linking all $I_{th}$ tables to their least different counterparts. From the base $I_{th}$ table, there can be multiple branches with each branch being generated based on similarity of the $I_{th}$ tables along that branch.

In some embodiments, all of the $I_{th}$ tables will be located in a linear or branched sequence using a single base $I_{th}$ table. In other embodiments, two or more base $I_{th}$ tables are selected (preferably, based on substantial differences between the base $I_{th}$ tables) and the remainder of the $I_{th}$ tables are associated with one of the base $I_{th}$ tables (for example, the most similar of the base $I_{th}$ tables) and linear or branched sequences of $I_{th}$ tables are generated using each of the base $I_{th}$ tables.

Once a linear or branched sequence of $I_{th}$ tables is generated, the individual $I_{th}$ tables in the sequence can be considered image frames and compressed into a compressed database using a MPEG compression algorithm that, instead of storing the individual $I_{th}$ tables in the compressed database, stores the base $I_{th}$ table(s) and then proceeds along each linear or branched sequence storing the difference between the current table and the preceding table. Again, a map is used to identify which data also the sequence corresponds to a particular $I_{th}$ table. When a particular $I_{th}$ table is subsequently needed, the compressed database and map are used to retrieve the $I_{th}$ table from the stored data.

Figures 9, 10:
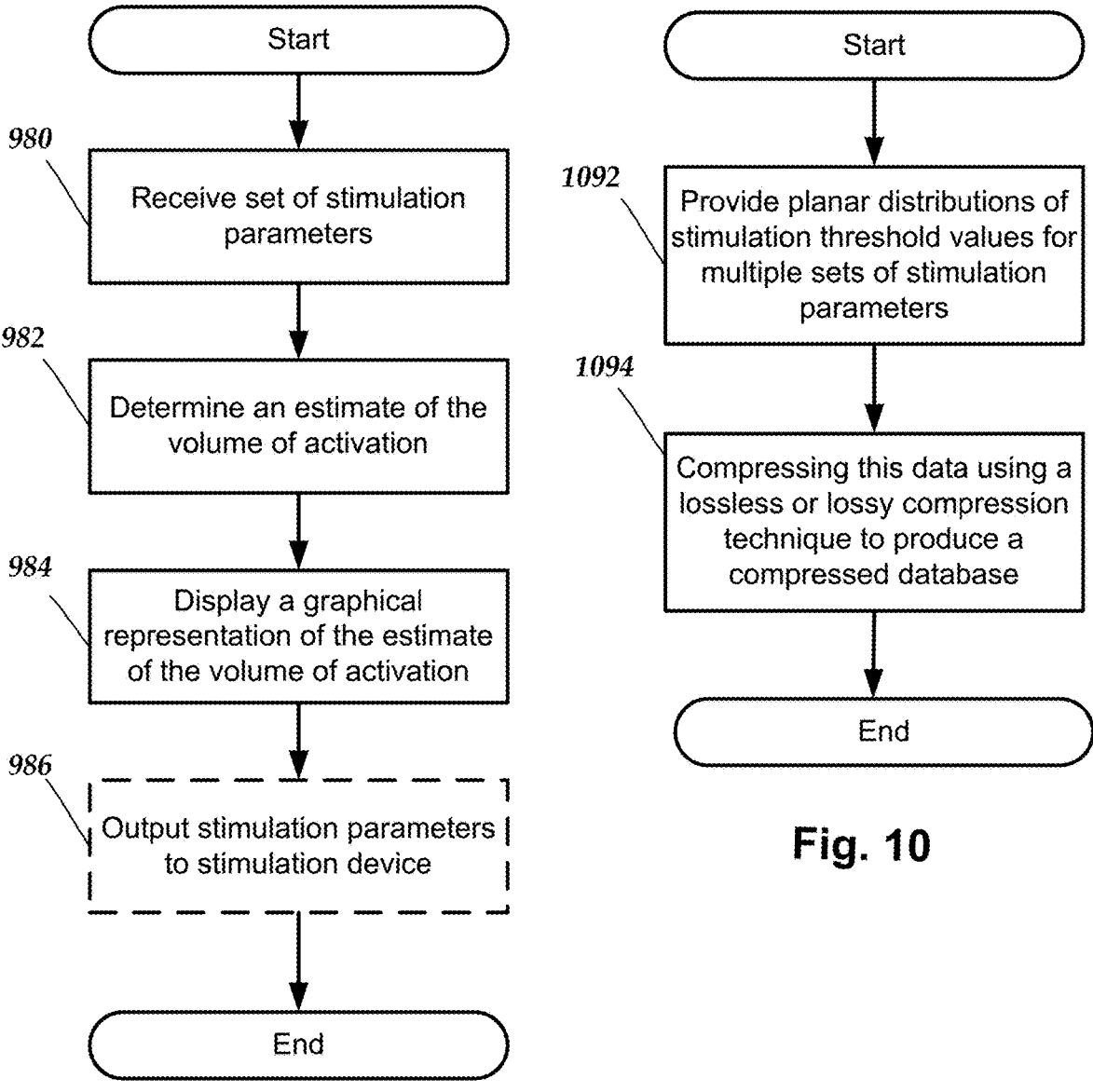

The lossless or lossy compressed databases described above can be stored in any suitable memory and then used to generate a volume of activation. FIG. 9 illustrates one method of estimating a volume of activation. In step 980, the system receives or is otherwise provided with a set of stimulation parameters with include a stimulation amplitude and a selection of one or more electrodes (referred to above as the "fractionalization") for delivery of the stimulation and may also include other parameters such as pulse width, frequency, or the like. In step 982, the system determines an estimate of the volume of activation using the set of stimulation parameters, the compressed database (such as database 760 or database 861), and the map (such as map 762 or map 862). For example, the set of stimulation parameters, compressed database, and map are used to obtain $I_{th}$ data corresponding to the set of stimulation parameters. For example, the $I_{th,unique}$ or $I_{th,approx.}$ tables of the compressed database can be identified for the designated fractionalization, pulse width, and frequency. The identified $I_{th,unique}$ or $I_{th,approx.}$ tables provided a spatial distribution in z, x, and θ of the threshold values for stimulation of neural elements. Using the stimulation amplitude and these threshold values, the system can estimate which regions will have neural elements that are stimulated for the given set of stimulation parameters.

In step 984, this estimated region can then be displayed graphically for the user. In optional step 986, the user may direct the system to output the stimulation parameters to a stimulation device, for example, the control module 514 of FIG. 5, that can produce stimulation signals for delivery to the patient via the lead electrodes. The stimulation device can receive the stimulation parameters and can then operate a stimulation program to deliver electrical stimulation to the patient using the stimulation parameters.

FIG. 10 illustrates one method of producing a compressed database. In step 1092, the system receives or produces planar distributions of stimulation threshold values for multiple sets of stimulation parameters. In step 1094, this data is compressed using one or more of the lossless or lossy compression methods described above to produce the compressed database.

A compressed database can be fully or partially decompressed. FIG. 11 illustrates one method of decompressing a compressed database. In step 1196, the compressed database and map is provided. In step 1198, the map is used to fully or partially compress the compressed database. For a lossless compressed database, this decompression regenerates the original database or a part of the original database. For a lossy compressed database, the decompression creates a new full or partial uncompressed database that utilizes only $I_{th,approx.}$ tables and, therefore, is an approximation of the original database. In some embodiments, only part of the compressed database is uncompressed. This part may be selected based on selections of certain stimulation parameter values. For example, the portion of the compressed database for a particular selection of electrodes or a particular selection of pulse width or frequency (or ranges of these values) may be decompressed. In some embodiments, this decompression may occur as part of a procedure for estimating a volume of activation (similar to step 982 of FIG. 9 except that a portion of the database is decompressed in this step). In some embodiments, decompression of different portions of the database may be performed sequentially during any suitable procedure. In some embodiments, the database may be compressed for storage or transfer to another device and then decompressed upon transfer to the other device or retrieval from storage.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

The above specification and examples provide a description of the invention and use of the invention. Since many embodiments of the invention can be made without departing from the spirit and scope of the invention, the invention also resides in the claims hereinafter appended.

What is claimed as new and desired to be protected by Letters Patent of the United States is:

1. A method for estimating a volume of activation around an implanted electrical stimulation lead for a set of stimulation parameters, the method comprising:

providing a database comprising a plurality of planar distributions of stimulation threshold values and an index identifying the planar distributions that correspond to angular locations around the implanted electrical stimulation lead based on a selection of one or more electrodes of the implanted electrical stimulation lead for delivery of stimulation, wherein each of the planar distributions represents a set of regions in a plane relative to the implanted electrical stimulation lead and each of the stimulation threshold values corresponds to a different one of the regions and comprises a stimulation amplitude that when applied to the selected one or more electrodes of the implanted electrical stimulation lead will stimulate tissue at the one of the regions corresponding to the stimulation threshold value;

receiving a set of stimulation parameters comprising a first stimulation amplitude and a first selection of one of more electrodes of the implanted electrical stimulation lead for delivery of the first stimulation amplitude;

determining an estimate of the volume of activation using the first stimulation amplitude, the first selection of one or more electrodes of the implanted electrical stimulation lead, and the database; and displaying a graphical representation of the estimate of the volume of activation.

2. The method of claim 1, wherein the database consists of the plurality of planar distributions, wherein each of the planar distributions is unique.

3. The method of claim 2, wherein the database is a lossless compressed database.

4. The method of claim 2, wherein the database is a lossy compressed database.

5. A system for estimating a volume of activation around an implanted electrical stimulation lead for a set of stimulation parameters, the system comprising:

a display; and a processor coupled to the display and configured to:

provide a database comprising a plurality of planar distributions of stimulation threshold values and an index identifying the planar distributions that correspond to angular locations around the implanted electrical stimulation lead based on a selection of one or more electrodes of the implanted electrical stimulation lead for delivery of stimulation, wherein each of the planar distributions represents a set of regions in a plane relative to the implanted electrical stimulation lead and each of the stimulation threshold values corresponds to a different one of the regions and comprises a stimulation amplitude that when applied to the selected one or more electrodes of the implanted electrical stimulation lead will stimulate tissue at the one of the regions corresponding to the stimulation threshold value;

receive a set of stimulation parameters comprising a first stimulation amplitude and a first selection of one of more electrodes of the implanted electrical stimulation lead for delivery of the first stimulation amplitude;

determine an estimate of the volume of activation using the first stimulation amplitude, the first selection of one or more electrodes of the implanted electrical stimulation lead, and the database; and output on the display a graphical representation of the estimate of the volume of activation.

6. The system of claim 5, wherein the selection of the one or more electrodes is characterized by at least one fractionalization parameter.

7. The system of claim 6, wherein the at least one fractionalization parameter comprises at least one of an axial position parameter, an angular direction parameter, or an angular spread parameter.

8. The system of claim 5, wherein the first selection of the one or more electrodes is characterized by at least one of an axial position parameter, an angular direction parameter, or an angular spread parameter.

9. The system of claim 5, wherein the index comprises a plurality of entries, wherein each of the entries is indexed to the selection of the one or more electrodes and an angular location around the implanted electrical stimulation lead.

10. The system of claim 9, wherein at least two of the entries of the index point to a same planar distribution.

11. The system of claim 10, wherein the at least two of the entries comprise a first entry indexed to a selection of a first one of the electrodes and a first angular location and a second entry indexed to a selection of a second one of the electrodes and a second angular location, wherein the first angular location and the second angular location differ by a first angle, wherein a location of the first one of the electrodes differs from a location of the second one of the electrodes by the first angle.

12. The system of claim 5, wherein the database consists of the plurality of planar distributions, wherein each of the planar distributions is unique.

13. The system of claim 12, wherein the database is a lossless compressed database.

14. The system of claim 12, wherein the database is a lossy compressed database.

15. A non-transitory computer-readable medium having computer executable instructions stored thereon that, when executed by at least one processor, cause the at least one processor to perform the instructions, the instructions comprising:

providing a database comprising a plurality of planar distributions of stimulation threshold values and an index identifying the planar distributions that correspond to angular locations around the implanted electrical stimulation lead based on a selection of one or more electrodes of the implanted electrical stimulation lead for delivery of stimulation, wherein each of the planar distributions represents a set of regions in a plane relative to the implanted electrical stimulation lead and each of the stimulation threshold values corresponds to a different one of the regions and comprises a stimulation amplitude that when applied to the selected one or more electrodes of the implanted electrical stimulation lead will stimulate tissue at the one of the regions corresponding to the stimulation threshold value;

receiving a set of stimulation parameters comprising a first stimulation amplitude and a first selection of one of more electrodes of the implanted electrical stimulation lead for delivery of the first stimulation amplitude;

determining an estimate of the volume of activation using the first stimulation amplitude, the first selection of one or more electrodes of the implanted electrical stimulation lead, and the database; and displaying a graphical representation of the estimate of the volume of activation.

16. The non-transitory computer-readable medium of claim 15, wherein the index comprises a plurality of entries, wherein each of the entries is indexed to the selection of the one or more electrodes and an angular location around the implanted electrical stimulation lead.

17. The non-transitory computer-readable medium of claim 16, wherein at least two of the entries of the index point to a same planar distribution.

18. The non-transitory computer-readable medium of claim 15, wherein the database consists of the plurality of planar distributions, wherein each of the planar distributions is unique.

19. The non-transitory computer-readable medium of claim 18, wherein the database is a lossless compressed database.

20. The non-transitory computer-readable medium of claim 18, wherein the database is a lossy compressed database.

* * * * *